(12) United States Patent
Lowery

(10) Patent No.: US 8,317,698 B2
(45) Date of Patent: Nov. 27, 2012

(54) METHOD OF MONITORING AN AUTOMATED POINT-OF-CARE FLUID TESTING SYSTEM

(75) Inventor: Michael G. Lowery, Wildwood, IL (US)

(73) Assignee: Hospira, Inc., Lake Forest, IL (US)

( * ) Notice: Subject to any disclaimer, the term of this patent is extended or adjusted under 35 U.S.C. 154(b) by 240 days.

(21) Appl. No.: 12/862,150

(22) Filed: Aug. 24, 2010

(65) Prior Publication Data

US 2011/0054276 A1 Mar. 3, 2011

Related U.S. Application Data

(60) Provisional application No. 61/238,284, filed on Aug. 31, 2009.

(51) Int. Cl.
*A61B 5/00* (2006.01)
(52) U.S. Cl. ...................................... 600/309
(58) Field of Classification Search .................... 600/309
See application file for complete search history.

(56) References Cited

U.S. PATENT DOCUMENTS

| | | | |
|---|---|---|---|
| 3,935,876 A | 2/1976 | Massie et al. |
| 4,857,050 A | 8/1989 | Lentz et al. |
| 5,303,585 A | 4/1994 | Lichte |
| 6,017,318 A | 1/2000 | Gauthier et al. |
| 6,396,583 B1 | 5/2002 | Clare |
| 7,254,425 B2 | 8/2007 | Lowery et al. |
| 7,364,562 B2 | 4/2008 | Braig et al. |
| 7,367,942 B2 | 5/2008 | Grage et al. |
| 2003/0045840 A1 | 3/2003 | Burko |
| 2004/0133166 A1 | 7/2004 | Moberg et al. |
| 2004/0193025 A1 | 9/2004 | Steil et al. |
| 2006/0187069 A1 | 8/2006 | Duan |
| 2006/0235353 A1 | 10/2006 | Gelfand et al. |
| 2007/0060872 A1 | 3/2007 | Hall et al. |
| 2007/0179436 A1 | 8/2007 | Braig et al. |
| 2007/0240497 A1 | 10/2007 | Robinson et al. |
| 2008/0065420 A1 | 3/2008 | Tirinato et al. |
| 2008/0097288 A1 | 4/2008 | Levin et al. |
| 2009/0069743 A1 | 3/2009 | Krishnamoorthy et al. |
| 2009/0156922 A1* | 6/2009 | Goldberger et al. ........... 600/364 |
| 2009/0156975 A1* | 6/2009 | Robinson et al. ............ 604/4.01 |
| 2009/0192367 A1* | 7/2009 | Braig et al. .................. 600/311 |
| 2009/0264720 A1* | 10/2009 | Torjman et al. ............... 600/322 |
| 2010/0217154 A1* | 8/2010 | Deshmukh et al. ........... 600/575 |

FOREIGN PATENT DOCUMENTS

JP 4322661 B2 7/2005

* cited by examiner

*Primary Examiner* — Rodney Fuller
(74) *Attorney, Agent, or Firm* — Michael R. Crabb

(57) ABSTRACT

A method of monitoring performance of a fluid testing system is provided. The method draws a fluid sample to the testing system using a pump. A voltage output of a sensor, such as an optical sensor, is generated. The voltage output of the optical sensor during the drawing is compared to an upper fluid volume drawn based voltage limit and a lower fluid volume drawn based voltage limit stored within a memory. The system is flushed with a flushing fluid using the pump to flush the flushing fluid from the testing system. The voltage output of the optical sensor during the flushing is compared to an upper fluid volume flushed based voltage limit and a lower fluid volume flushed based voltage limit stored within the memory. An alert generates if at least one of the voltage output during the drawing of the fluid sample is outside of voltage limits.

20 Claims, 29 Drawing Sheets

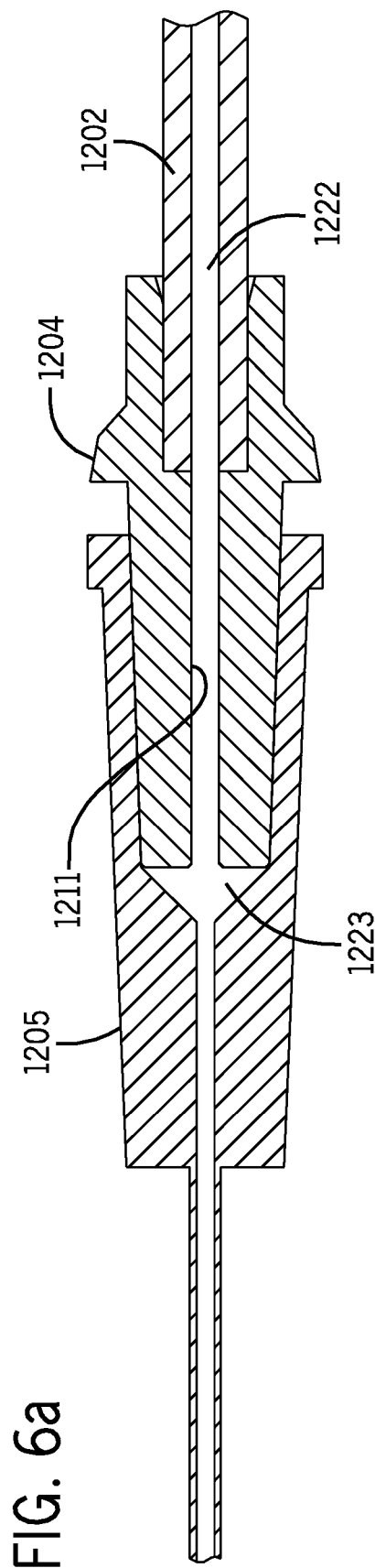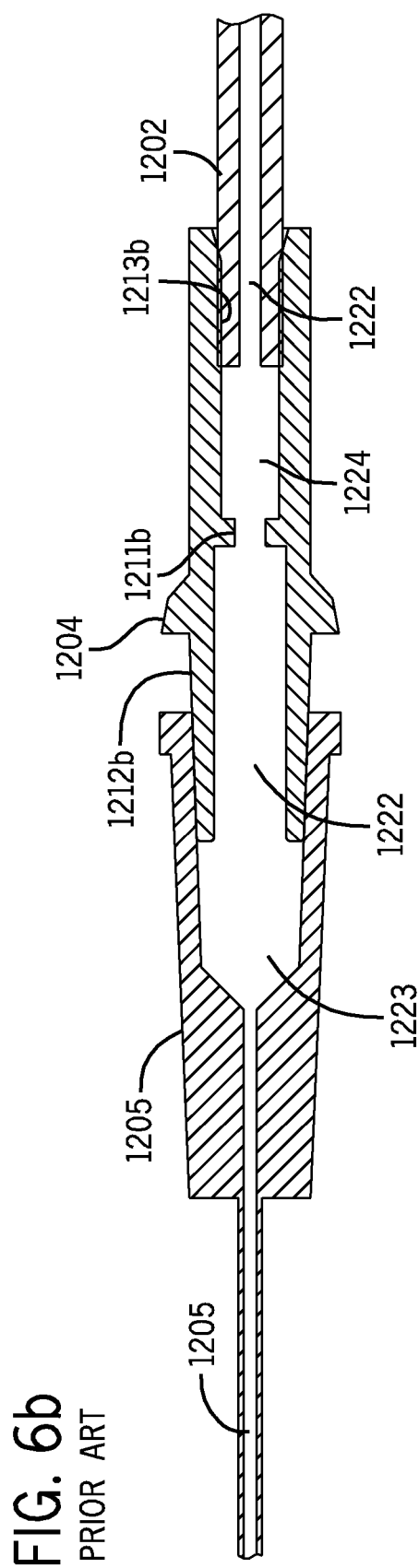
FIG. 6a
FIG. 6b PRIOR ART

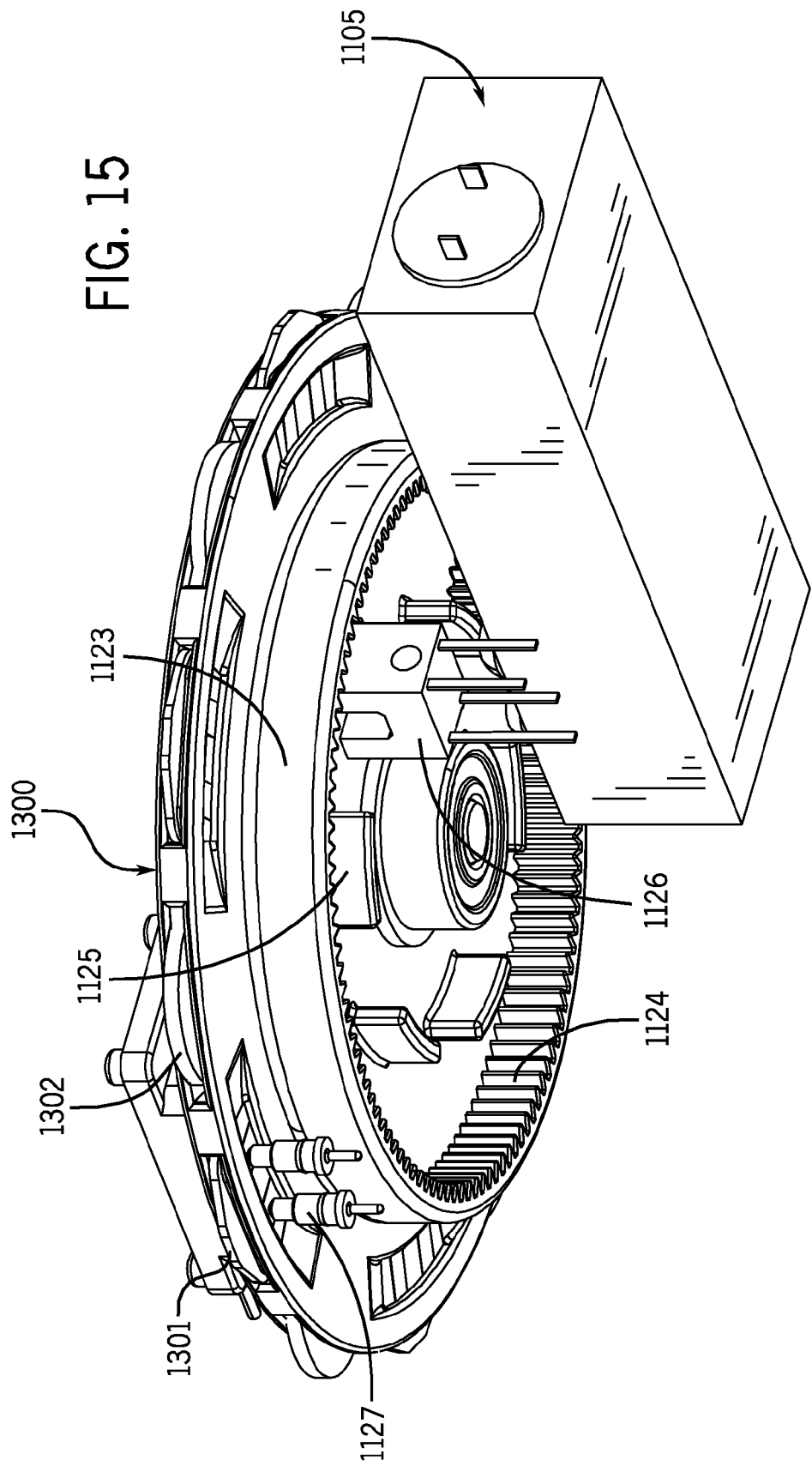

METHOD OF MONITORING AN AUTOMATED POINT-OF-CARE FLUID TESTING SYSTEM

CROSS REFERENCE TO RELATED APPLICATIONS

This application claims the benefit of U.S. Provisional Application No. 61/238,284, filed Aug. 31, 2009.

TECHNICAL FIELD

The present invention generally relates to an automated repetitive point-of-care fluid testing device for gathering information about the quantity of certain analytes in a patient's blood, and/or properties of the patient's blood. The present invention utilizes a system that includes both an in-line testing region, and an off-line testing region. The present invention utilizes sensor output limits to indicate potential malfunctions during testing.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

Many patients who are connected to a medical pump may be receiving an acute level of care, such as that provided in a hospital intensive care unit ("ICU"). A patient in an ICU is likely suffering from a very serious medical problem, that often is life threatening. As such, frequent monitoring of the patient's condition is required, including regular blood tests to determine quantities of analytes present in the blood, and to determine properties of the patient's blood. Examples of analytes in a patient's blood that may require monitoring include: glucose, lipid profiles (e.g., cholesterol, triglycerides, LDL and HDL), microalbumin, hemoglobin $A_{IC}$, fructose, lactate, bilirubin, and other known analytes. One property of a patient's blood that may require monitoring is the coagulation rate of the blood. Since coagulated blood cannot be returned to the patient, coagulation tests are typically done off-line in a remote laboratory and take considerable time to complete.

Unfortunately, caregivers in an ICU are very busy and may be unavailable to collect a sample from a patient at an appointed time, due to the needs of other patients. Further, equipment needed to perform tests on a sample in a location remote from the patient, such as in a lab, may also be unavailable or unable provide results in a timely manner. Additionally, many patients in an ICU are in such grave condition that only a limited amount of blood may safely be drawn from the patient. Furthermore, a caregiver may have difficulty in finding an appropriate location to collect blood samples from the patient.

Failing to properly monitor analyte levels or other properties of the patient's blood can lead to adverse effects for the patient. Thus, an automated system to collect and analyze a sample from the patient from a give collection site at preset intervals may improve the level of care the patient receives. Based on results of the testing, the patient's medication may be adjusted, or other treatments for the patient may be deemed proper or necessary. Further, it is desirable to be able to perform different types of tests on the sample, including in-line testing, and off-line testing. Still further, it is desirable to test a small fluid sample. For in-line testing it is desirable to draw, test, and re-infuse the blood sample in a time period short enough to prevent any significant clotting in the sample. Still further, it is desirable to monitor that performance of the automated system is within established performance limits. Therefore, a need exists for an automated point-of-care in-line testing unit that performs both in-line and off-line testing, as desired in a flexible, programmable, timely, safe, and efficient manner.

SUMMARY

According to one process, a method of monitoring performance of a fluid testing system having a sensor, a patient connection adapted to connect the system to a patient to collect a fluid sample, a pump, a processor in communication with a memory, and a flushing fluid connection adapted to connect the system to a flushing fluid to flush the system after a fluid test is provided. The method draws a fluid sample from the patient via the patient connection using a pump of the testing system to draw the fluid sample from the patient to the testing system. A voltage output of a sensor, by way of example and not limitation an optical sensor, indicative of a fluid present at the sensor is generated. The voltage output of the sensor during the drawing of the fluid sample is compared to an upper fluid volume drawn based voltage limit and a lower fluid volume drawn based voltage limit stored within a memory in communication a processor. The method flushes the system with a flushing fluid using the pump of the testing system to flush the flushing fluid from the testing system. The voltage output of the sensor during the flushing of the flushing fluid is compared to an upper fluid volume flushed based voltage limit and a lower fluid volume flushed based voltage limit stored within the memory in communication with the processor. An alert is generated if at least one of the voltage output during the drawing of the fluid sample is outside of the lower fluid volume drawn based voltage limit and the upper volume drawn based voltage limit and the voltage output during the flushing of the flushing fluid is outside of the lower fluid volume flushed based voltage limit and the upper fluid volume flushed based voltage limit.

According to another process, a method of generating voltage output limits for a fluid draw of a fluid testing system having a sensor, a patient connection adapted to connect the system to a patient to collect a fluid sample, a pump, a processor in communication with a memory is provided. The method draws a known quantity fluid sample using a pump of the testing system to draw the fluid sample to the testing system. A plurality of voltage outputs of a sensor are generated indicative of a fluid present at the sensor periodically during the drawing of the fluid sample. An upper voltage limit is calculated utilizing a forward exponential moving average of the plurality of voltage outputs and a positive offset value. The method calculates a lower voltage limit utilizing a reverse exponential moving average of the plurality of voltage outputs and a negative offset value.

According to a further process, a method of generating voltage output limits for a fluid flush of a fluid testing system having a sensor, a patient connection adapted to connect the system to a patient to collect a fluid sample, a pump, a processor in communication with a memory is provided. The method flushes a known quantity of fluid from the fluid testing system using a pump of the testing system to flush the fluid. A plurality of voltage outputs of a sensor are generated indicative of a fluid present at the sensor periodically during the flushing of the fluid. An upper voltage limit is calculated utilizing a reverse exponential moving average of the plurality of voltage outputs and a positive offset value. The method calculates a lower voltage limit utilizing a forward exponential moving average of the plurality of voltage outputs and a negative offset value.

BRIEF DESCRIPTION OF THE DRAWINGS

FIG. 6a is a sectional view showing the connector of FIG. 6 assembled with distal tubing and a catheter;

FIG. 6b is a sectional view showing a prior art standard Luer connector assembled with distal tubing and a catheter;

FIG. 15 is a bottom pictorial view of a rotating mechanism for the disposable off-line testing disk for use with the testing system shown in FIG. 4;

DETAILED DESCRIPTION

Figure 1:
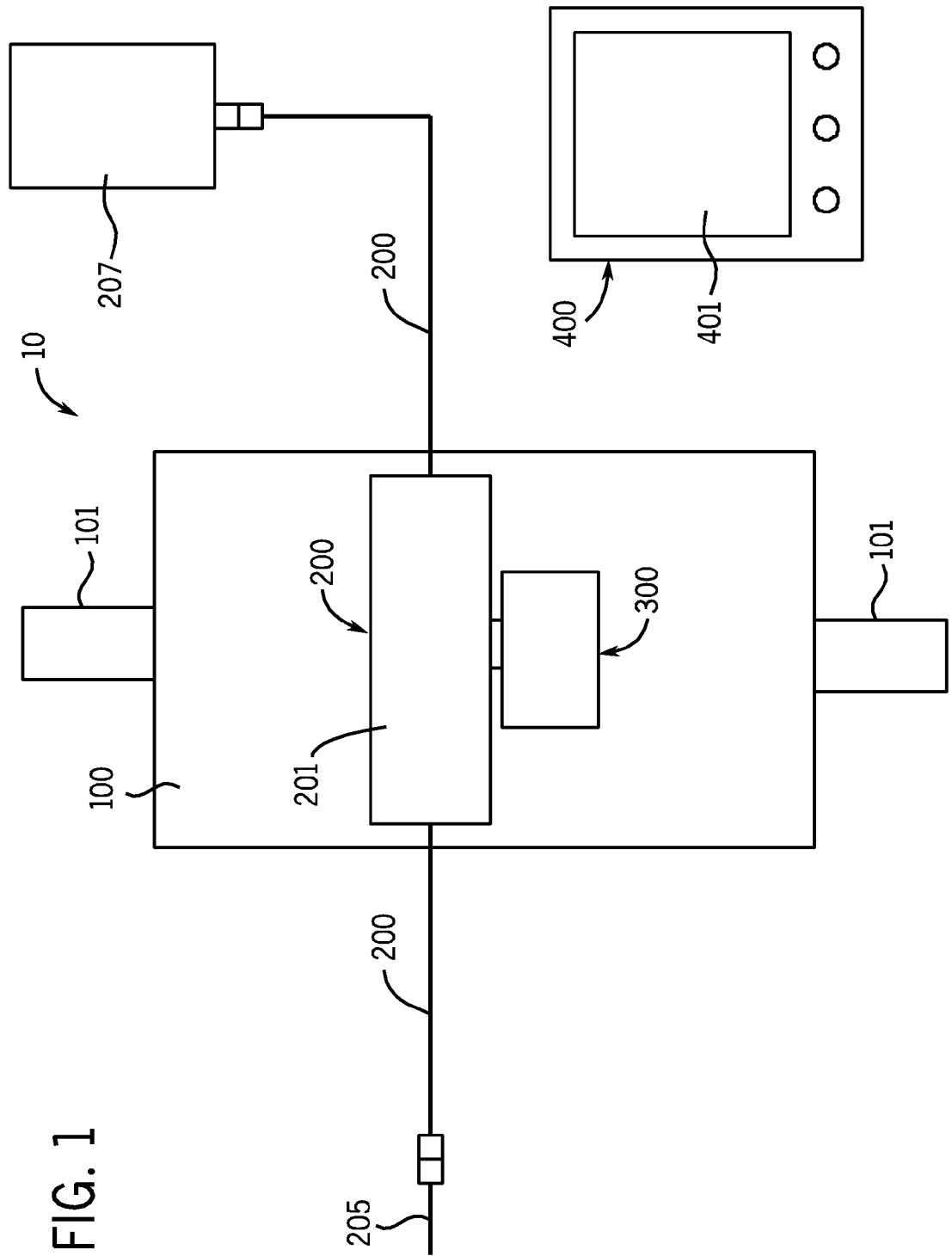
FIG. 1 is a schematic view of a testing system according to one embodiment.

While this invention is susceptible of embodiments in many different forms, there is shown in the drawings and will be described herein an example of the invention. The present disclosure is to be considered as an example of the principles of the invention. It is not intended to limit the broad aspect of the invention to the examples illustrated.

FIG. 1 is a schematic representation of a point-of-care testing system 10 comprising a main body 100 adapted to be attached to a patient via two attachment straps 101. The attachment straps 101 may attach the main body 100 of testing device 10 to the patient via a VELCRO® fastener or other similar temporary attachment methods, such as an adhesive, that allows the attachment straps 101 to be removably attached to each other to secure the main body 100 to a desired location. For example, it may be convenient to attach the main body 100 of the system 10 to the patient's arm. In such a situation the attachment straps 101 would be wrapped around the patient's arm in such a manner to secure the main body 100 to the patient. According to one embodiment the main body 10 is relative small, having a volume of less than about twenty (20) cubic inches, and weighing less than about two (2) pounds. It is further contemplated that the main body 100 may additionally be contoured to be applied to a specific body part of a patient, such as a forearm, leg, or abdomen. While such a contour is not required, it may improve patient comfort. It is contemplated that in many cases the forearm will serve as a beneficial mounting location based on the ease of access and the number of blood vessels in the forearm. The main body 100 may be reusable, in that it may be used on more than one patient, by following proper cleaning and sterilization techniques before being used with another patient. It is further contemplated that the main body 100 can be releasably secured to a bed rail, pole, or other support structure near the patient's bedside rather than being worn by the patient.

The testing system 10 additionally comprises a disposable portion 200. The disposable portion, described in more detail below, is adapted to be used with only one single patient and may require periodic replacement on that patient.

A catheter 205 is adapted to be placed into a blood vessel of the patient. The catheter 205 may be a standard 20 Gauge×2 inch catheter, or other commonly available catheter appropriate for the blood vessel utilized. Depending on the application, the blood vessel selected may be an artery or a vein. If blood gas levels, or properties that may vary based on blood gas levels, are to be monitored the blood vessel selected will be an artery. A vein may be used if blood gases are not of interest or do not affect the property or properties to be determined using the testing system. The main body 100 of the testing system is preferably located near the location where the catheter 205 is placed into the blood vessel, in order to minimize the volume of blood needed for a sample. It is contemplated that the main body 100 will be positioned within one hundred centimeters (100 cm), more preferably within about twenty centimeters (20 cm), of the location the catheter 205 enters the blood vessel.

Figure 2:
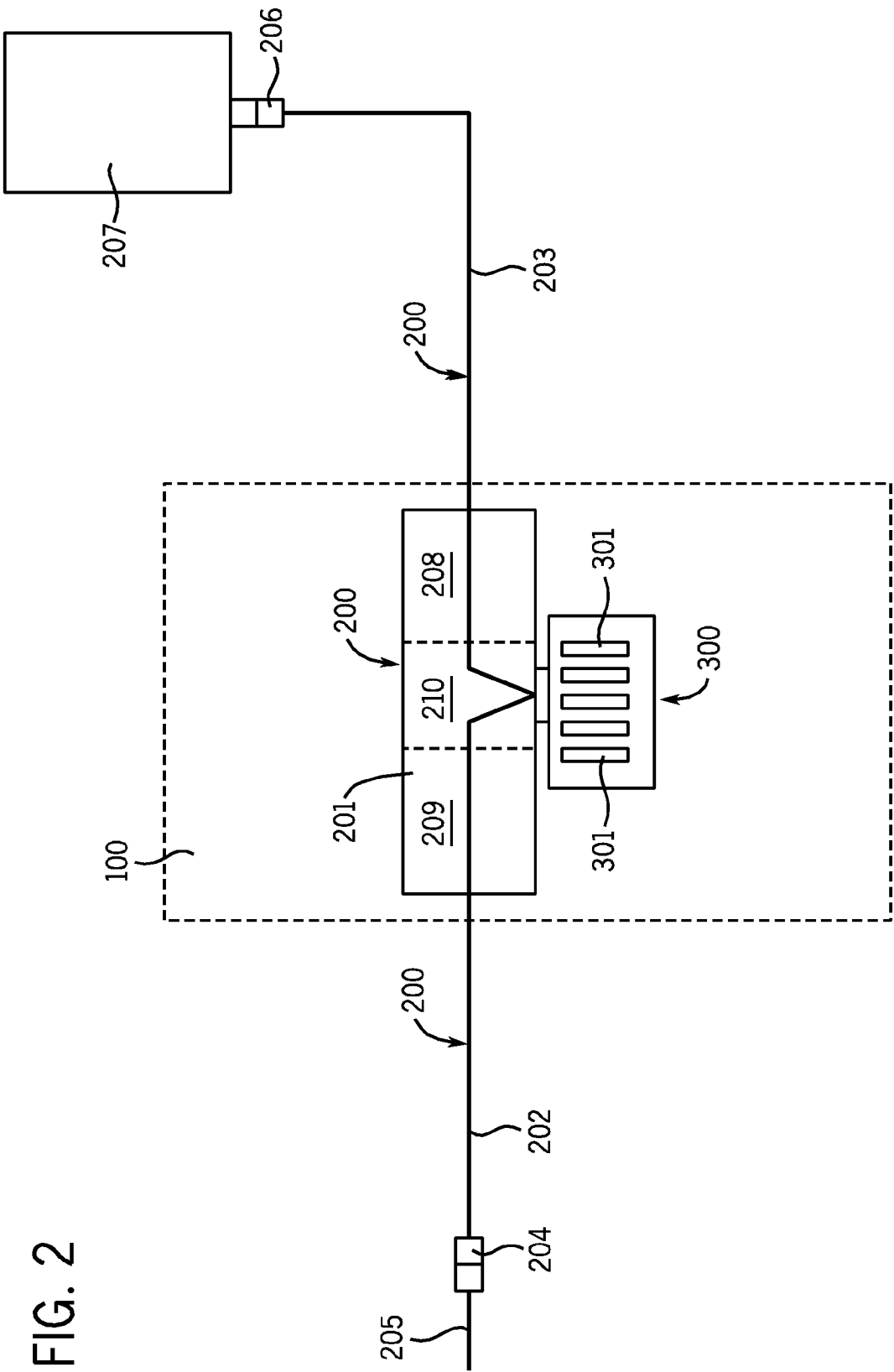
FIG. 2 shows a more detailed schematic view of disposable portions of a testing system according to the embodiment of FIG. 1.
Figure 3:
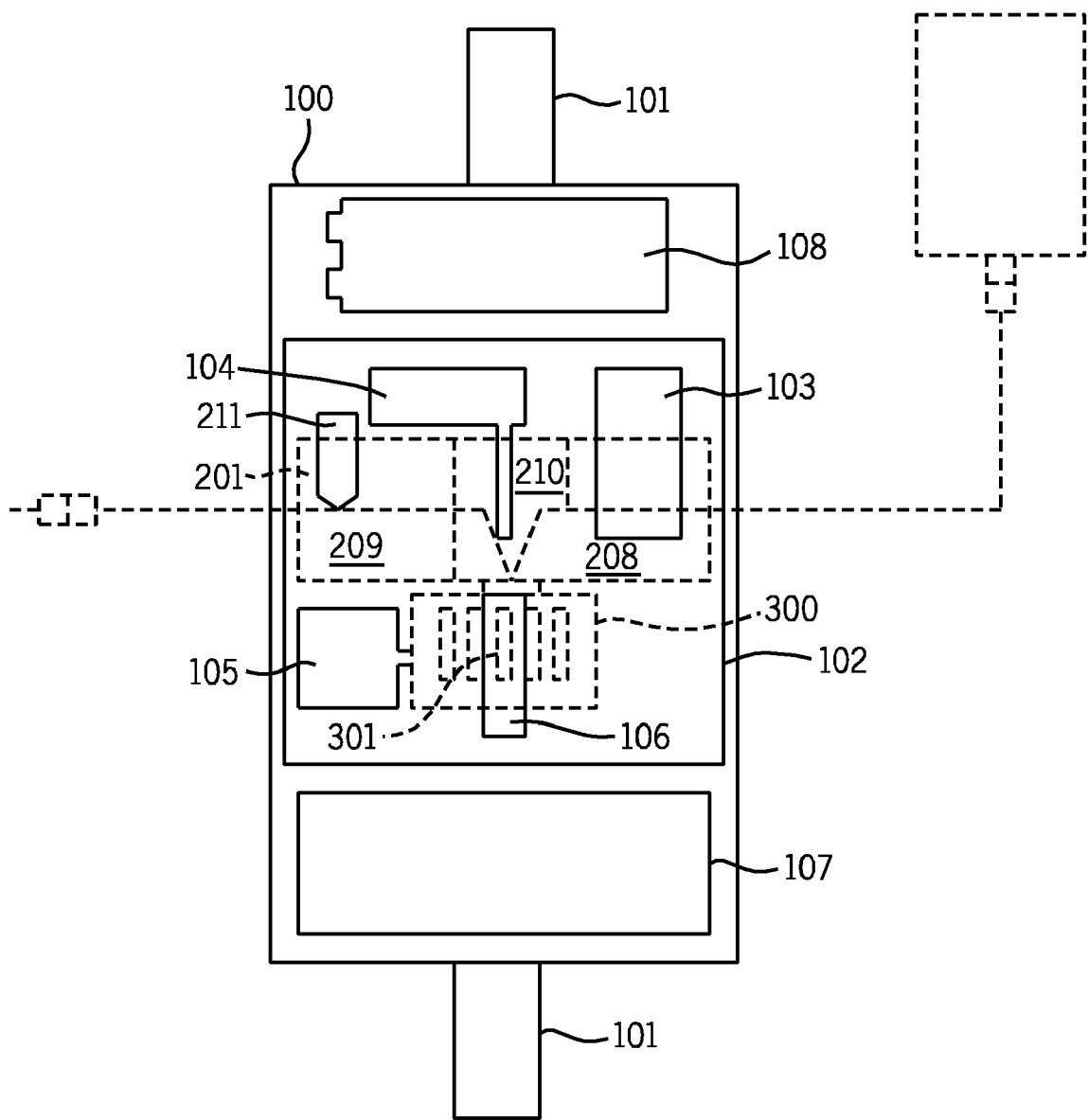
FIG. 3 shows a more detailed schematic view of reusable portions of the testing system according to the embodiment of FIG. 1.

As shown in FIGS. 1-3, the main body 100 houses, removably receives, or operatively couples with two disposable portions, a primary fluid routing portion 201 and a secondary fluid routing portion 300. The primary fluid routing portion 201 has an in-line testing region 209 that includes an in-line sensor 211. The secondary fluid routing portion 300 includes a secondary fluid routing portion 301. The primary fluid routing portion 201 and the secondary fluid routing portion 300 are selectively connectable in fluid communication through a fluid transfer region 210. As used herein, in-line testing refers to blood testing where substantially all of the blood that enters the testing portion may be returned to the patient, while off-line testing is used to refer to blood testing where the blood will not be returned to the patient. As shown in FIG. 1, the secondary fluid routing portion 300 is connected to the primary fluid routing portion 201. Thus, the blood that enters the secondary fluid routing portion 300 of the system 10 was initially within the primary fluid routing portion 201. Only a relatively small fraction of the blood within the primary fluid routing portion 201 is transferred into the secondary fluid routing portion 300. For example, but by now way of limitation, when the sample is five hundred microliters (500 μL) the portion transferred to the secondary fluid routing portion could be fifty microliters (50 μL).

The testing system 10 additionally comprises a flush solution reservoir 207. The flush solution reservoir 207 contains a flush solution adapted to flush the blood out of the system 10 prior to the initiation of a test, or to reinfuse the blood back to the patient following the completion of a test. The flush solution may be a medically-approved water-based solution including but not limited to saline, dextrose and water, potassium chloride, electrolytes, etc. The flush solution additionally may be used to prime the testing system 10 prior to connecting the system to the patient. The system 10 may need to be primed to ensure that air is not present in fluid passages of the system 10. It is additionally contemplated that the flush solution may contain one or more substances used to calibrate an in-line test sensor 209 (FIG. 2) of the primary fluid routing portion 201. The initial volume of flush solution within the flush solution reservoir 207 should be sufficient to prime the testing system 10 and operate the system 10 for a period of from about 12 hours to about 96 hours. According to some embodiments the initial volume of flush solution may range from about 100 mL to about 1000 mL. It is additionally contemplated according to some embodiments that some portion of the flush solution within the reservoir 207 may be used to keep the patient's blood vessel open at the site of the catheter 205.

The primary fluid routing portion 201 and the secondary fluid routing portion 300 are adapted to be placed within the main body 100 of the testing system 10 by a caregiver at the start of care of the patient, or when the portions 201, 300 need replacement. It is contemplated that the portions 201, 300 may be used for a period of up to 96 hours prior to replacement.

Additionally shown in FIG. 1 is control device 400. The main body 100 of the testing system 10 communicates with a control device 400. The control device 400 has a user interface 401 to allow the caregiver to view results of tests performed automatically by the system 10 and to set the frequency of testing. The user interface 401 may be a touch screen, or other known user interface types, to allow the caregiver to easily communicate with the system 10. The control device 400 may be an infusion pump, such as a SYMBIQ® infusion system or pump by Hospira, Inc., that is being used to provide medication or other fluids to a patient. Wireless communication between the main body 100 of the testing system 10 and the control device 400 is preferred, as a wireless system does not require the caregiver to route communication cables from the body 100 to the control device 400. However, it is contemplated that in some situations the communications between the main body 100 and the control device 400 will be carried via a wire or cable. Alternatively, it is contemplated that the main body 100 of the testing system 10 can have its own integral control device and/or user interface to display test results and accept operational commands. The test results over a particular selectable time period of interest can be displayed in graphical or other suitable format.

Turning now to FIG. 2, additional details of the disposable portion 200 of the system 10 are shown. The disposable portion 200 provides a continuous fluid passage from the patient's blood vessel via the catheter 205 through the main body 100 of the testing system 10 and to the fluid reservoir 207. The disposable portion 200 has a distal end at the catheter 205 that is inserted into the patient's blood vessel. The catheter 205 connects to a distal connecter 204 that is also connected to a first fluid line portion 202. The first fluid line portion 202 runs from the distal connector 204 to the primary fluid routing portion 201 within the main body 100 (shown in broken lines in FIG. 2) of the testing device 10. The first fluid line portion 202 is a flexible tubing that may be conveniently routed by the caregiver. The first fluid line portion 202 may be from about 10 cm to about 50 cm in length, and preferably has an internal volume of less than about two-hundred microliters (200 μL).

The distal connector 204 may be of any suitable leak-proof design, such as a Luer type connector, that preferably has a fluid volume of less than about twenty microliters (20 μL) when the connector 204 is connected to the catheter 205 and the first fluid line portion 202.

The disposable portion 200 additionally comprises a second fluid line portion 203. The second fluid line portion 203 runs from the primary fluid routing portion 201 within the main body 100 to a proximal connecter 206 connected to the flush solution reservoir 207. It is contemplated that the second fluid line portion 203 may be significantly longer than the first fluid line portion 202 in order to conveniently locate the flush solution reservoir 207 away from the patient, such as on a fixed or portable bedside pole. It is contemplated that the internal volume of the second fluid line portion 203 may be more than ten times the internal volume of the first fluid line portion 202. Providing the second fluid line portion 203 with much greater internal volume than the first fluid line portion 202 reduces the likelihood of contaminating the flush solution reservoir with blood that has entered the system 10. The proximal connector 206 may be a Leur type connector, a tapered spike, needle cannula, or any other known type of connector for accessing the fluid in the reservoir 207.

As shown in FIG. 2, the primary fluid routing portion 201 may be divided into three main regions, a fluid pumping region 208, a fluid testing region 209, and a fluid transfer region 210. The primary fluid routing portion 201 may be in the form of a disposable cassette containing the pumping region 208, the fluid testing region 209, and the fluid transfer region 210. The total volume of fluid within the primary fluid routing portion 201 is preferably less than three hundred microliters (300 µL). The fluid testing region 209 can be an in-line fluid testing region.

The pumping region 208 of the primary fluid routing portion 201 is a fluid passage that interacts with a pump contained in the main body 100. The pumping region 208 may have an elastic region, such as a silicone membrane or polymeric tubing, which engages a peristaltic-type pump, or other type pump, within the body 100. The pumping region 208 allows for bi-directional flow within the primary fluid routing portion 201, i.e., fluid may flow either away from the patient or back towards the patient, depending upon the operation of the pump. The pumping region 208 further is adapted to stop all flow within the primary fluid routing portion 201 when the pump is stopped. Flow may be stopped in order to perform certain fluid testing within the in-line fluid testing region 209 of the primary fluid routing portion 201.

The fluid testing region 209 is a fluid passage having at least one integrated sensor adapted to determine information about the patient's blood. The information may include determining the level of certain analytes within the blood, such as the patient's blood glucose level. The sensor disposed within the testing region 209 can be a single use sensor, but is more preferably a reusable sensor capable of performing a plurality of blood sample analyte measurements over the life of the disposable portion 200 or the primary fluid routing portion 201. The testing region 209 may contain a sensor, or sensors, capable of measuring blood glucose, blood gases, electrolytes, lactate, and other analytes. The sensor, or sensors, of the testing region 209 may utilize electrochemical, optical, colorimetric, or other known technologies for measuring blood analytes. The testing region 209 additionally is adapted to electrically communicate results of testing to the rest of the system 10, such as by electrodes or other wired or wireless circuitry.

Still referring to FIG. 2, the fluid transfer region 210 of the primary fluid routing portion 201 allows a small volume of blood within the primary fluid routing portion 201 to be deposited, expressed, or otherwise transferred to the secondary fluid routing portion 300. The blood, or other fluid, that is transferred to the secondary fluid routing portion 300 never reenters the primary fluid routing portion 201, but remains in secondary fluid routing portion 300. The fluid transfer region 210 allows the secondary fluid routing potion 300 to be utilized to perform testing that takes a longer period of time to perform, or requires a reaction that makes the blood unsuitable to return to the patient. A non-limiting example of a test to be performed in the secondary fluid routing portion 300 is a blood coagulation test, as coagulated blood should not be returned to the patient.

It is contemplated that the small volume of blood transferred through the fluid transfer region 210 to the secondary fluid routing portion 300 should be less than about twenty microliters (20 µL) per transfer. It is contemplated that a transfer through the transfer region 210 of the primary fluid routing portion 201 to the secondary fluid routing portion 300 may be made every time a blood sample is taken from the patient via the system 10. It is further contemplated that some tests utilizing the secondary fluid routing portion 300 may not need to be taken as frequently as tests utilizing the testing region 209 of the primary fluid routing portion 201, and in such a situation a portion of only selected blood samples would need to be transferred through the transfer region 210 to the secondary fluid routing portion 300.

In some embodiments, a plurality of transfers through the transfer region 210 to the secondary fluid routing portion 300 and secondary fluid routing portion 301 may be made per blood sample. For instance, a small amount of flushing solution may first be transferred to the secondary fluid routing portion 300 prior to any blood being pumped into the primary fluid routing portion 201. Then blood from the patient may be transferred from the primary fluid routing portion 201. Finally, a third transfer may provide flushing solution into the secondary fluid routing portion 300 as the flushing solution is used to pump the blood from the primary fluid routing portion back into the patient.

The transfer region 210 of the primary fluid routing portion 201 may have a valve, a fluid circuit, or other known fluid transfer device that can be activated by a mechanism located remotely or within the main body 100 in order to facilitate the transfer of fluid from the primary fluid routing portion to the secondary fluid routing portion. The transfer region 210 must be designed to prevent leakage of fluid, prevent the introduction of air, and prevent the introduction of microbes during the transfer from the primary fluid routing portion 201 to the secondary fluid routing portion 300. Additionally, the transfer region 210 must permit a plurality of transfers to occur successively, without becoming either clogged or adversely affected by fluids previously transferred during the lifespan of the primary fluid routing portion 201.

The disposable secondary fluid routing portion 300 is in fluid communication with the primary fluid routing portion 201 via the transfer region 210. The secondary fluid routing portion 300 has an off-line testing portion 301 comprising one or more, more preferably an array or plurality of spaced apart single use diagnostic sensors 301. However, it is contemplated that the invention can be used with multiple use sensors as well. The sensors 301 may be, but are not limited to, blood coagulation sensors, such as for use with a PT, aPTT, or ACT blood coagulation test. The fill volume for each sensor 301 is preferably less than about twenty microliters (20 µL). The secondary fluid routing portion 300 is adapted to sequence the sensors 301 such that each sensor 301 can receive a volume of blood transferred from the transfer region 210 of the primary fluid routing portion 201, while also preventing the sample volume from contacting other sensors in the array. The sensors 301 may be sequenced by a rotating platform, a linear translating platform, a fluid circuit with valves that operate sequentially, or other known sequencing methods. The sample transferred into the secondary fluid routing portion 300 may reach an individual sensor 301 via capillary action, or by pumping from the pumping region 208 of the primary fluid routing portion 201 for a brief time period, such as less than ten seconds.

The secondary fluid routing portion 300 additionally is adapted to electrically communicate results of testing on a test sensor 301 to the rest of the system 10, such as by electrodes, or other wired or wireless circuitry. The secondary fluid routing portion 300 may also be positioned within the main body 100 in order to receive heat from a heater 106 within the main body 100, such that any tests performed in the secondary fluid routing portion are performed under proper temperature conditions.

The secondary fluid routing portion 300 is adapted to contain from about 1 to about 36 test sensors 301, depending on the required frequency of off-line testing. Due to the fluid transfer region 210, if the secondary fluid routing portion 300 contains single use sensors 301 or supports a different frequency of testing that the primary fluid routing portion 201, the secondary fluid routing portion can be removed from the main body 100 independently of the primary fluid routing portion 201, without having to remove the system 10 from the patient. Thus, a caregiver may replace the secondary fluid routing portion 300 while the testing system 10 is still connected to the patient and without the need to change the primary fluid routing portion 201. This is particularly useful if the number of off-line test sensors 301 that may be placed in the secondary fluid routing portion 300 is small, or if a caregiver determines that a different analyte level or blood property needs to be monitored on the patient.

Turning next to FIG. 3, the reusable main body 100 of the testing system 10 is shown in more detail. The main body 100 is adapted to be used on a plurality of patients over a number of years. It is contemplated that the main body 100 may be used for up to three years or longer with proper care. Proper sterilization and cleaning procedures must be followed between uses of the main body 100 on different patients. The main body 100 comprises an opening 102 for receiving one or more of the disposable portions 201, 300, a pump 103, a fluid transfer mechanism 104, an off-line sensor indexer 105, a heating element 106, a controller 107, and a power source 108.

The main body 100 has an access door 111 (not shown) that allows a caregiver to access the opening 102, such as to replace the primary fluid routing portion 201, or the secondary fluid routing portion 300 (shown in broken lines). Typically a caregiver will use the access door 111 to place a primary fluid routing portion 201 and the secondary fluid routing portion 300 into the body 100 at the beginning of use of the system 10 on a particular patient, and to remove the testing portions 201, 300 from the body 100 at the conclusion of use of the system 10 on the patient. Additionally, the access door 111 may be positioned so as to be utilized to replace the secondary fluid routing portion 300 while the system is connected to the patient.

The pump 103 is a mechanism, such as a peristaltic pump, piezo element, magnetic field, or other known pump type, that causes fluid to flow inside of the pumping region 208 of the primary fluid routing portion 201. Preferably, the pump 103 is bi-directional or capable of causing fluid to flow in either direction, away from the patient or towards the patient, within the testing system 10. However, a uni-directional pump can be used with appropriate valving to achieve bi-directional flow. The flow rate provided by the pump 103 must be sufficient to allow testing operations to be completed within a two minute period by drawing blood into the system, performing in-line testing, transferring blood for off-line testing, and re-infusing the blood remaining in the primary fluid routing portion back into the patient. The pump 103 is also adapted to completely stop flow within the primary fluid routing portion 201, such as when an in-line test is performed in the in-line testing region 209.

Still referring to FIG. 3, the fluid transfer mechanism 104 may include a motorized cam, a piston, a magnet, or other known methods to cause the transfer region 210 of the primary fluid routing portion 201 to transfer fluid from within the primary fluid routing portion to the secondary fluid routing portion 300.

The sensor indexer 105 may be a rotational motor or linear motor, or other type device that positions an individual sensor 301 relative to the transfer region 210 to receive fluid from the primary fluid routing portion 201 via the transfer region 210.

The heating element 106 provides thermal energy to regulate the temperature of at least one of the sensors 301 of the secondary fluid routing portion 300 to help ensure accurate test results. For example, the heating element may regulate the temperature of the sensor 301 to about 37° C. during the period of testing for a blood coagulation sensor. It is contemplated that the heating element 106 may be stationary and the sensor indexer 105 will position the individual sensor 301 near the heating element 106. Alternatively, the heating element 106 may be movable so as to be positioned near the individual sensor 301 or both the heating element 106 and the sensor 301 may be movable for that purpose. It is additionally contemplated that a plurality of heating elements 106 may be provided such that every individual sensor 301 of the secondary fluid routing portion 300 is provided with a heating element 106.

A reusable fluid sensor 211 may additionally be incorporated into the main body 100 and is functionally engaged with the in-line testing region 209 of the disposable portion 200. The fluid sensor 211 produces a signal, such as an electric signal, that varies in strength based on the composition of the fluid in the in-line testing region 209. The fluid sensor 211 may be used for determining, for example, if a blood sample has been drawn into the in-line testing region 209, and subsequently, if the blood sample has been fully flushed from the in-line testing region 209 by a flush solution after an in-line diagnostic test has been performed. The fluid sensor 211 may also be used for detecting the presence of an unwanted air pocket inside the test region. The fluid sensor 211 can thereby add a measure of efficacy to the testing system 10 by providing an ability to confirm proper flow of blood and flush solution inside the disposable portion 201 while ensuring that no air is present.

The reusable fluid sensor 211 may comprise an optical sensor, such as a paired LED emitter and photo-detector unit, or some other reusable sensor capable to distinguish between blood, flush solution, and air within n a sensing zone of the disposable portion 200. Alternatively, the fluid sensor 211 may be a suitable disposable design that is integral to the disposable portion 201 and comes into contact with the fluid, such as an electrochemical or electrically conductive sensor, which is disposed along with the cassette upon completion of use on a patient. Furthermore, the fluid sensor 211 may alternatively be located elsewhere in the disposable portion 201 or elsewhere along the disposable set 200, however, it is preferred to locate the sensor 211 in close proximity to where the blood sample is tested for diagnostic analysis.

The controller 107 is adapted to operate and functionally coordinate all of the electro-mechanical components, such as the pump 103, the fluid transfer mechanism 104, the off-line sensor indexer 105, and the heating element 106 of the testing system 10. The controller 107 also allows the main body 100 to communicate with the control device 400 (FIG. 1) to report test results from the testing system 10 or to obtain instructions from the caregiver entered via the control device 400.

The power source 108 of the main body 100 is a battery, such as a lithium ion battery, that provides sufficient power to operate the system for an extended period of time, such as between eight and seventy-two hours. Alternatively, the power source 108 may be an A/C power source. If the power source 108 is a battery, it may be rechargeable or disposable. It is contemplated that if a rechargeable battery is used for the power source 108, the power source may be recharged while the system 10 is in use on a patient.

Figure 4:
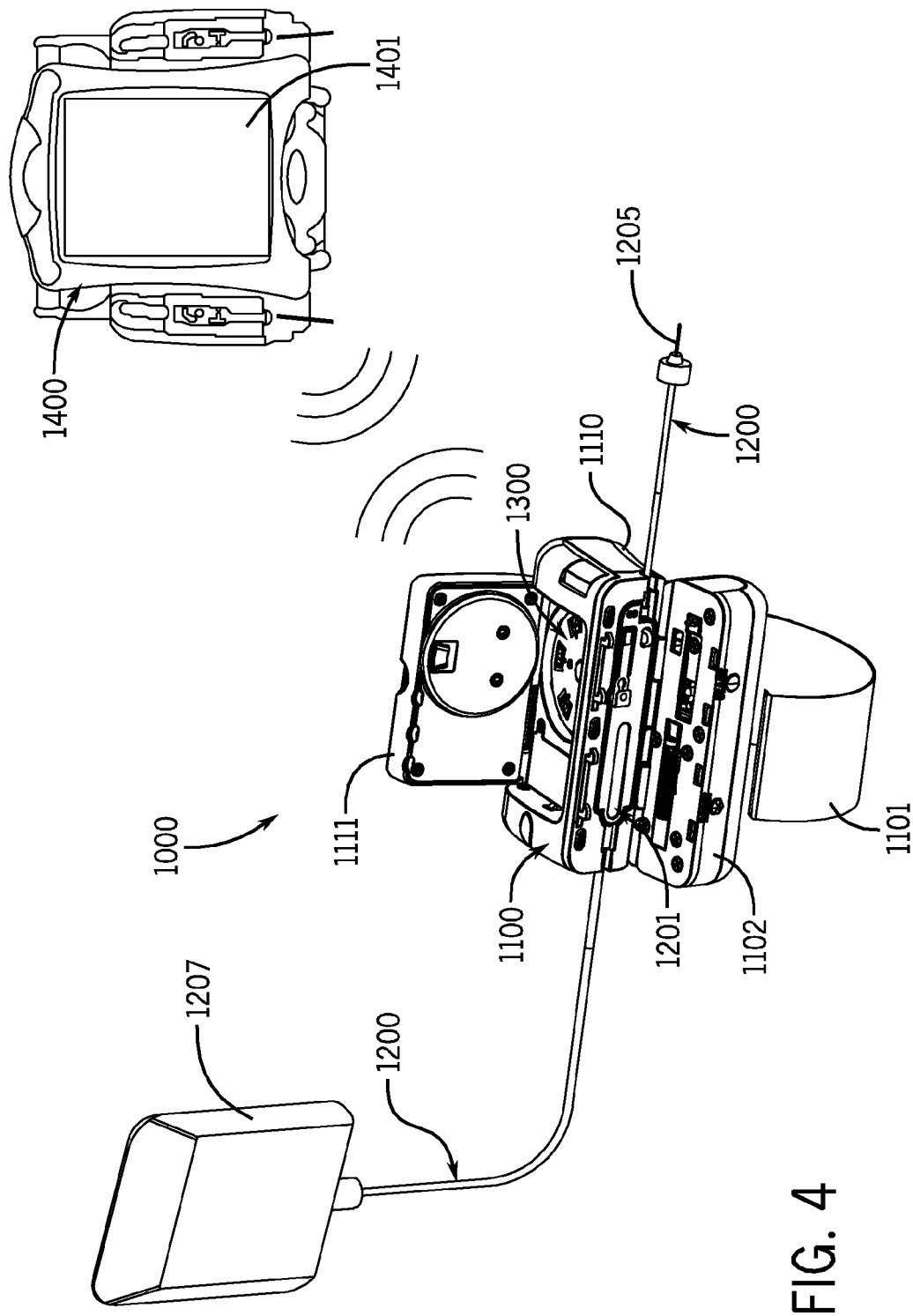
FIG. 4 is a pictorial view illustrating a testing system according to a further embodiment.

Referring now to FIG. 4, a more detailed embodiment of a point-of-care testing system 1000 is shown. The testing system 1000 comprises a reusable main body 1100, a disposable assembly 1200, including the primary fluid routing portion 1201 and the secondary fluid routing portion 1300, described in greater detail in connection with FIG. 5, a catheter 1205 to connect to a blood vessel of a patient, a flush solution reservoir 1207, and a control device 1400. The testing system 1000 shown in FIG. 4 is adapted to perform an in-line blood glucose test and an off-line blood coagulation test; however, it is contemplated that other analytes or blood properties could be tested as described in connection with FIGS. 1-3.

The main body 1100 has a primary fluid routing portion access door 1102 and a secondary fluid routing portion access door 1111. The primary fluid routing portion access door 1102 allows a care giver to access the primary fluid routing portion 1201, while the secondary fluid routing portion access door 1111 allows a caregiver to replace the secondary fluid routing portion 1300 without having to worry about disrupting the primary fluid routing portion 1201. The main body 1110 shown in FIG. 4 measures approximately 4.75"×3.75"× 1.7" giving a total volume of approximately 30 cubic inches. The main body 1100 has a total weight of about 0.75 lbs. A strap 1101 with a VELCRO® type connector allows the main body 1100 to be releasably secured to a patient, such as by attaching the strap 1101 around a patient's arm or leg.

The control device 1400 shown in FIG. 4 is a SYMBIQ® infusion system or pump from Hospira. The control device 1400 has a touch screen user interface 1401 to allow the caregiver to enter instructions for the testing system 1000 and to view results of tests performed by the testing system 1000. For flexibility in locating the components and reduction of wires at the bedside, the control device 1400 and the main body 1100 communicate wirelessly in the embodiment shown in FIG. 4, although a wired connection would also suffice.

Figure 5:
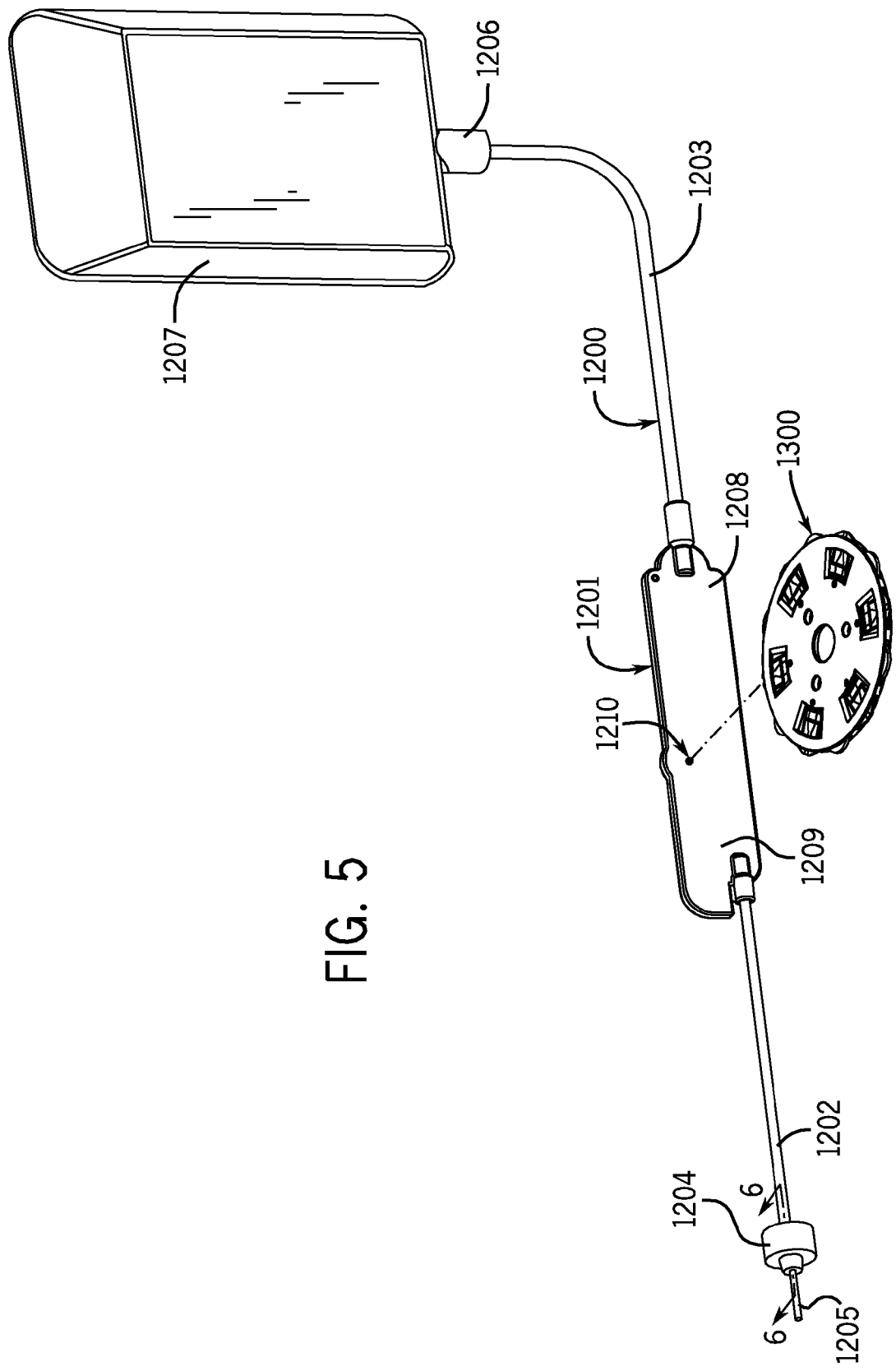
FIG. 5 is a pictorial view illustrating disposable components of the testing system according to the embodiment of FIG. 4.

FIG. 5 illustrates the disposable portions 1200, 1300 of the testing system 1000. The disposable portion 1200 provides the main fluid path of the testing system 1000. The disposable portion 1200 has the catheter 1205 at a distal end and the flush fluid reservoir 1207 at a proximal end. The catheter 1205 connects to a distal connector 1204. The distal connector 1204 also connects to a first fluid line portion or distal tubing 1202. The first fluid line portion 1202 runs from the distal connector 1204 to the primary fluid routing portion 1201. The first fluid line portion 1202 has a length of about 25 cm, and an inner diameter of about 0.030", giving the first fluid line portion 1202 a relatively small internal volume of 114 µL.

Figure 6:
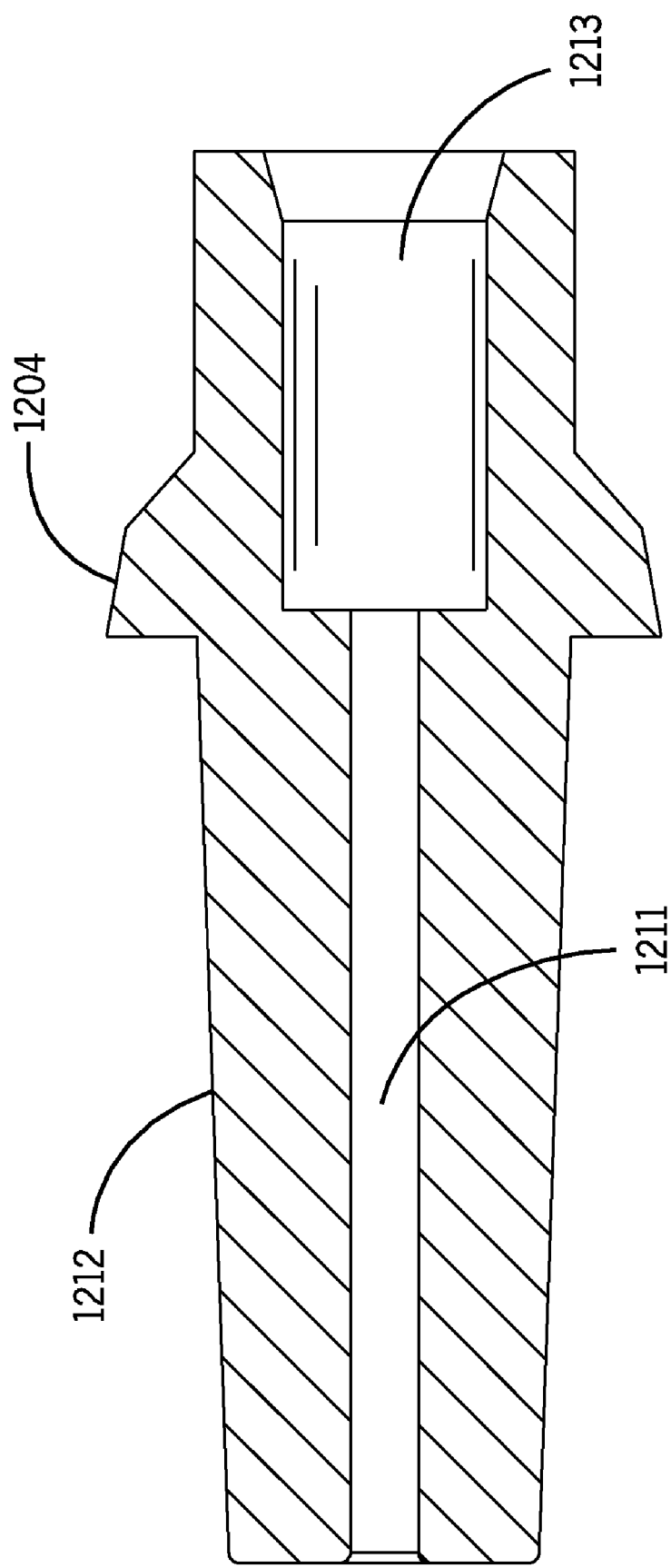
FIG. 6 is a sectional view of a connector taken along line 6-6 of FIG. 5.

As shown in FIGS. 6a and 6b, the distal connector 1204 is a low-volume distal connector. The low volume of the distal connector 1204 is obtained by providing a bore 1211 having a 1 cm length and a 0.030" diameter, providing a volume of about 5 µL. As best seen in FIG. 6a, the outer surface 1212 of the distal connector is designed to be completely inserted into the catheter 1205, thereby eliminating any excess fluid volume in the catheter 1205 caused by incomplete insertion. The diameter of the bore 1211 matches the diameter of the bore 1222 of the distal tubing 1202. Further, a receptacle 1213 is sized and shaped to allow a complete insertion of the distal tubing 1202 into the distal connector 1204, eliminating any excess volume or dead space caused by incomplete insertion of the distal tubing 1202. Thus, the low volume distal connector 1204 of FIGS. 6 and 6a offers improvements over a prior art Luer type connector shown in FIG. 6b by reducing the internal volume of the fluid flow path between the blood vessel and the primary fluid routing portion 1201 and eliminating dead spaces where fluid may tend to stagnate. In the connector 1204b of FIG. 6b, the bore 1211b does not match the bore 1222 of the distal tubing 1202, the outer surface 1212b is not designed to be completely inserted into the catheter 1205, and the receptacle 1213b is not sized and shaped to allow complete insertion of the distal tubing 1202. This causes dead spaces or locations, generally designated at 1222, 1223, and 1224 where blood may collect and resist flushing back into the patient following in-line testing. The connector 1204 of the present invention provides a substantially smooth, continuous, uninterrupted fluid flow path that is free from dead spaces or locations where blood may collect and resist flushing back into the patient. Blood is not allowed to stagnate in the lines, posing health risks to the patient or caregiver and possibly skewing results of subsequent tests.

Referring back to FIG. 5, the primary fluid routing portion 1201 has a pumping region 1208, a testing region 1209, and a fluid transfer region 1210. The fluid transfer region is aligned with the secondary fluid routing portion 1300 to provide a sample to a test sensor 1301 (FIG. 9) of the secondary fluid routing portion 1300. The primary fluid routing portion 1201 has an internal flow path with a volume of about 175 µL. Thus, the primary fluid routing portion 1201 and the first fluid line portion 1202 combine to have a volume of about 295 µL. In order to ensure that a proper blood sample is obtained, approximately two to four times this volume of blood must be removed from the patient; hence, between 600 and 1200 µL, of blood is required from the patient to perform a test. However, a majority of this blood will be infused back to the patient.

The primary fluid routing portion 1201 connects to a second fluid line portion 1203 that also connects to a proximal connector 1206 at the flush fluid reservoir 1207. The second fluid line portion has a length of about 90 cm and an internal diameter of about 0.054", providing an internal volume of about 1330 µL.

Figure 7:
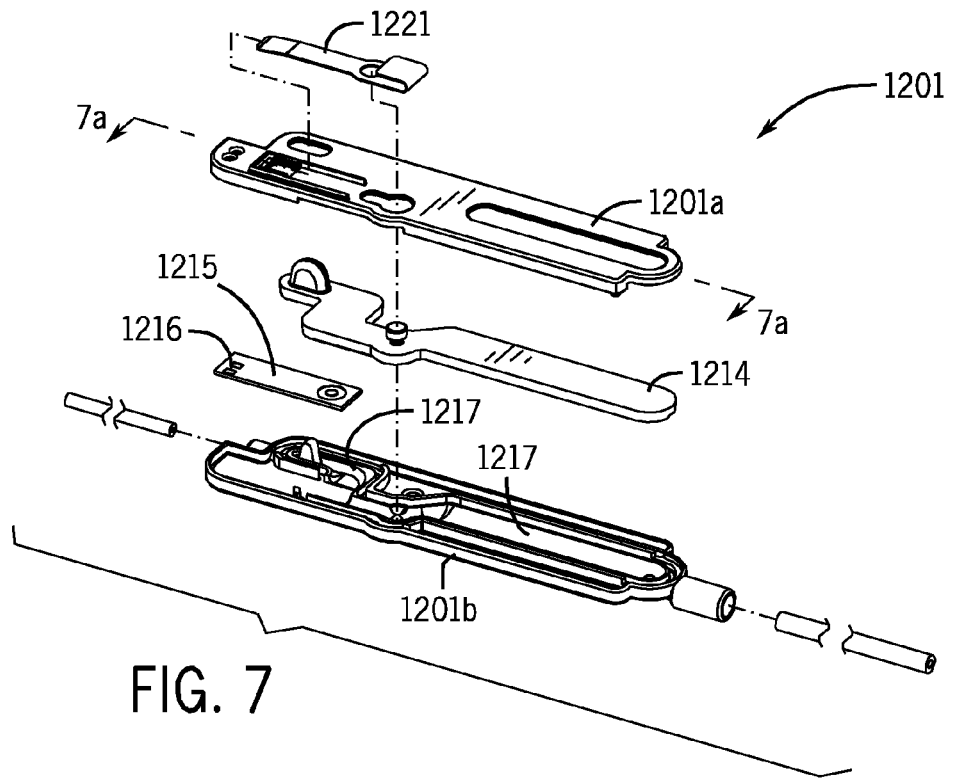
FIG. 7 is an exploded view illustrating a disposable testing cassette for use with the testing system according to the embodiment of FIG. 4.

Turning now to FIG. 7, an exploded view of the primary fluid routing portion 1201 is provided. In this embodiment, the primary fluid routing portion 1201 has a lid 1201a and a base 1201b. A flexible silicone diaphragm 1214 seals the primary fluid routing portion from fluid leakage, as well as preventing air or other outside contaminants from entering the primary fluid routing portion 1201. An in-line test sensor 1215 is provided in the primary fluid routing portion 1201 to measure the concentration of glucose within the blood that enters the primary fluid routing portion 1201. The test sensor 1215 includes electrodes 1216 that are exposed outside of the primary fluid routing portion 1201 to provide the results from the test sensor 1215 to the system 1000. The sensor 1215 is a thick-film design having a glucose-oxidase reagent that is reusable for up to 1000 test cycles over a 30 day period. The primary fluid routing portion 1201 additionally forms a fluid channel 1217 running the length of the primary fluid routing portion 1201.

In addition to the in-line test sensor 1215, the primary fluid routing portion 1201 has a fluid sensing zone 1225. Fluid that enters and exits the primary fluid routing portion 1201 passes through the fluid sensing zone 1225. It is contemplated that the fluid sensing zone 1225 is an optically transparent material, such as, for example, a clear polycarbonate polymeric material. The fluid sensing zone 1225 is located near, and generally proximal to, the in-line test sensor 1215, to allow an identification to be made of fluid within the primary fluid routing portion 1201 and nearing the test sensor 1215. The close proximity of the fluid sensing zone 1225 to the in-line test sensor 1215 allows the testing system 1000 to determine that a desired fluid to be sampled is in contact with the test sensor 1215.

Figure 7A:
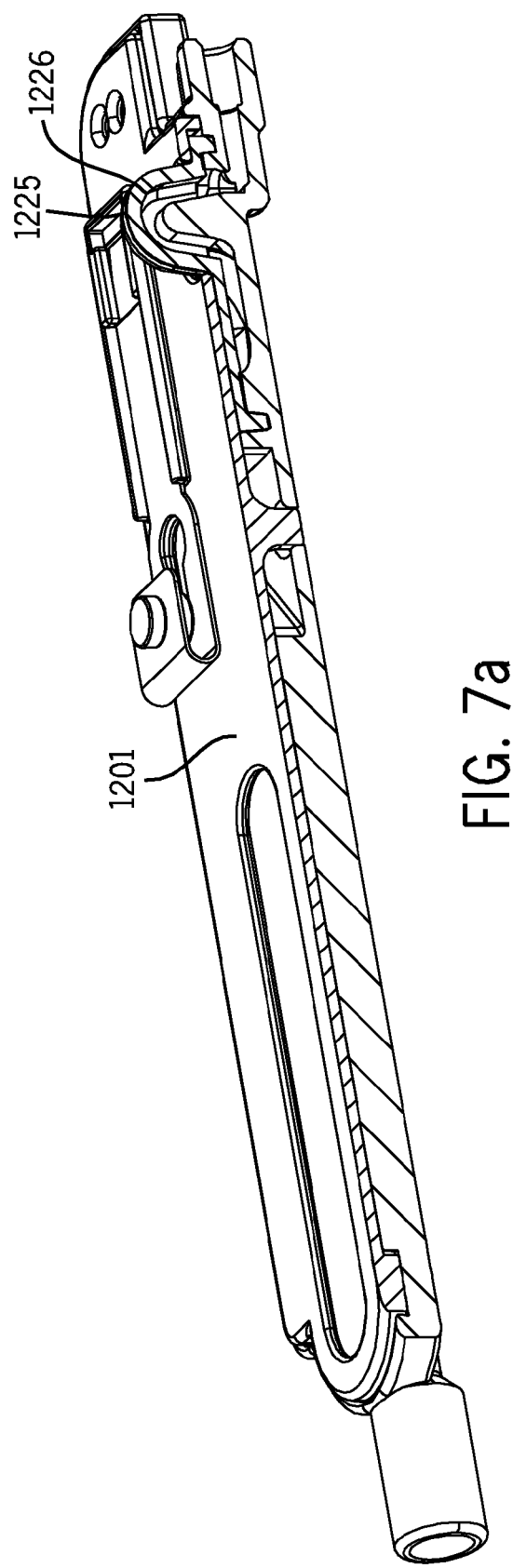
FIG. 7a is a cross-section view taken along line 7a-7a of FIG. 7.

Turning now to FIG. 7*a*, a sectional view taken through line 7*a*-7*a* of FIG. 7 is shown. FIG. 7*a* shows a raised fluid channel portion 1226 of the fluid channel 1217 within the fluid sensing zone 1225. Fluid within the fluid channel 1217 that enters the fluid sensing zone 1225 passes through the raised fluid channel 1226. The raised fluid channel 1226 allows an optical sensor (1227 FIG. 7*b*) to transmit light through the fluid sensing zone 1225 and generate an output used to determine what type of fluid is present within the fluid sensing zone 1225. The raised fluid channel portion 1226 extends beyond, generally higher, than the remainder of the fluid channel 1217, and the in-line test sensor 1215.

Figure 7B:
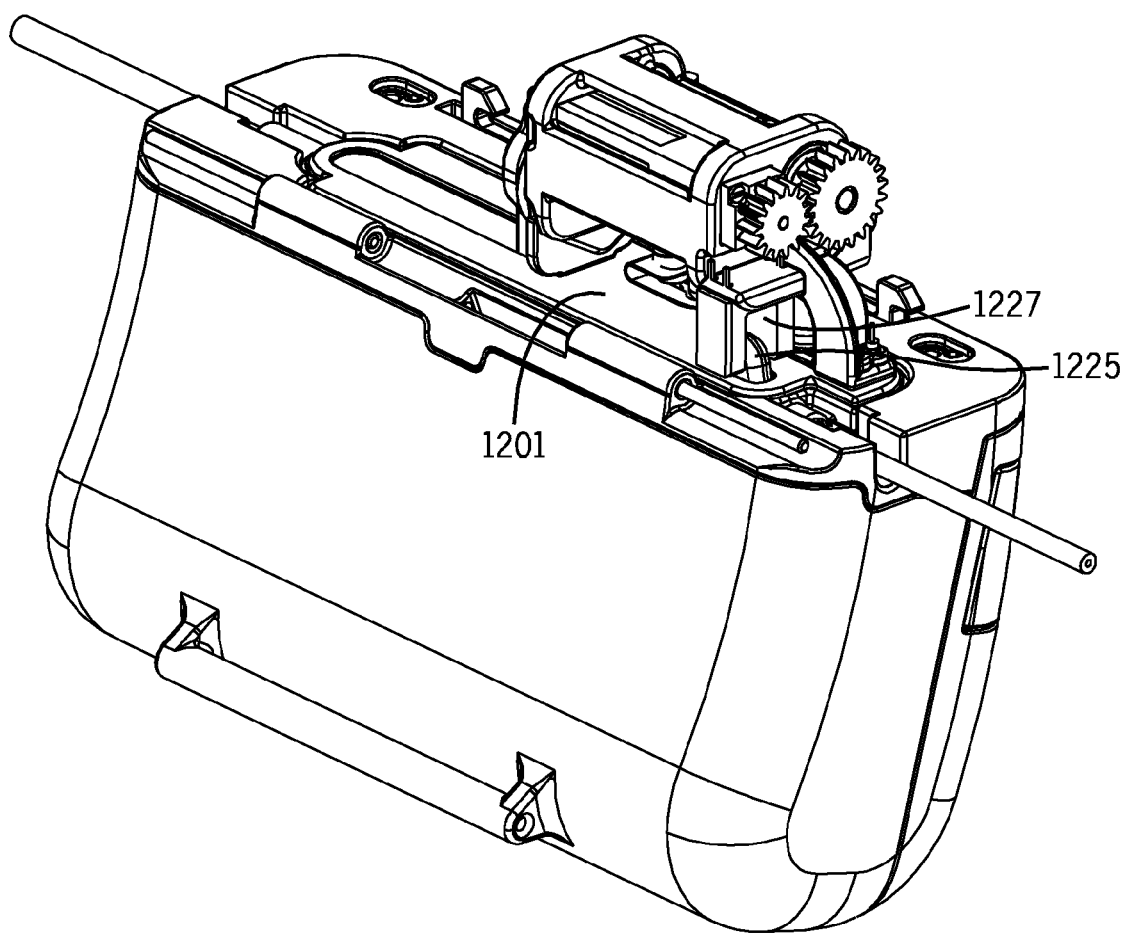
FIG. 7b is pictorial view illustrating a testing system according to yet a further embodiment.

FIG. 7*b* shows an arrangement of the fluid sensing zone 1225 and an optical sensor 1227. The optical sensor 1227 is contained within the main body 1100. It is contemplated that the optical sensor 1227 may be located within the primary fluid routing portion access door 1102. The optical sensor 1227 positions around the fluid sensing zone 1225 when the primary fluid routing portion 1201 is within the main body 1100 and the access door 1102 is closed. The access door 1102 has been removed from FIG. 7*b* for greater clarity. The optical sensor 1227 may be an LED type sensor. That is, light is emitted from an LED of the optical sensor 1227, the light passes through the fluid sensing zone 1225, and the light is detected by an optical detector of the optical sensor 1227. The optical detector of the optical sensor 1227 generates an output related to the intensity of the light received by the optical sensor 1227.

Various fluids that are typically found within the fluid sensing zone 1225 have distinct optical properties such that the output of the optical sensor 1227 for the various fluids within the sensing zone 1225 are distinguishable. Light is altered by refraction, scattering, reflection, and absorption as it passes through a fluid present in the sensing zone 1225 as it passes from the LED to the optical detector of the optical sensor 1227. Put another way, the intensity of the light that reaches the optical detector of the optical sensor 1227 allows a determination to be made of the fluid, blood, flush solution, air, or some other fluid, present within the sensing zone 1225.

The output of the optical sensor 1227 may then be compared to stored light intensity profiles to allow a determination of the identity of the fluid within the sensing zone 1225. For example, a light intensity profile for blood and a light intensity profile for flush solution may be stored on a memory. An algorithm executed by a processor compares the output generated by the optical sensor 1227 with stored light intensity profiles to determine the identity of the fluid present in the sensing zone 1225. Additionally, a processor may determine that the output generated by the optical sensor 1227 is not consistent with any stored pattern, and alert a caregiver that a malfunction has occurred, such as an abnormal fluid flow condition, or the presence of an air slug within the line.

Figure 8A:
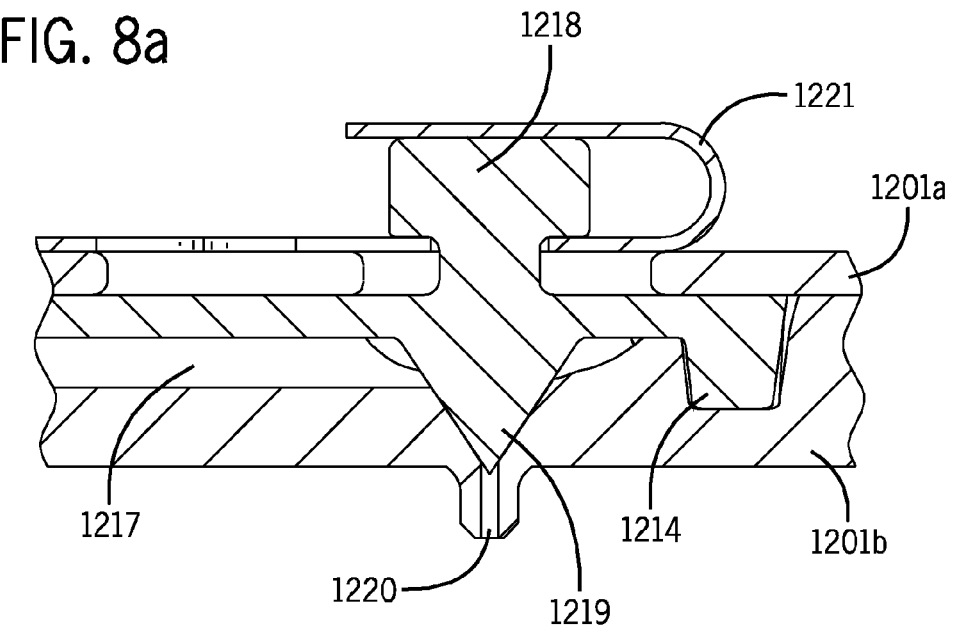
FIG. 8a is a cross-section view taken along line 8-8 of FIG. 7 depicting a valve portion of the cassette in a closed position.
Figure 8B:
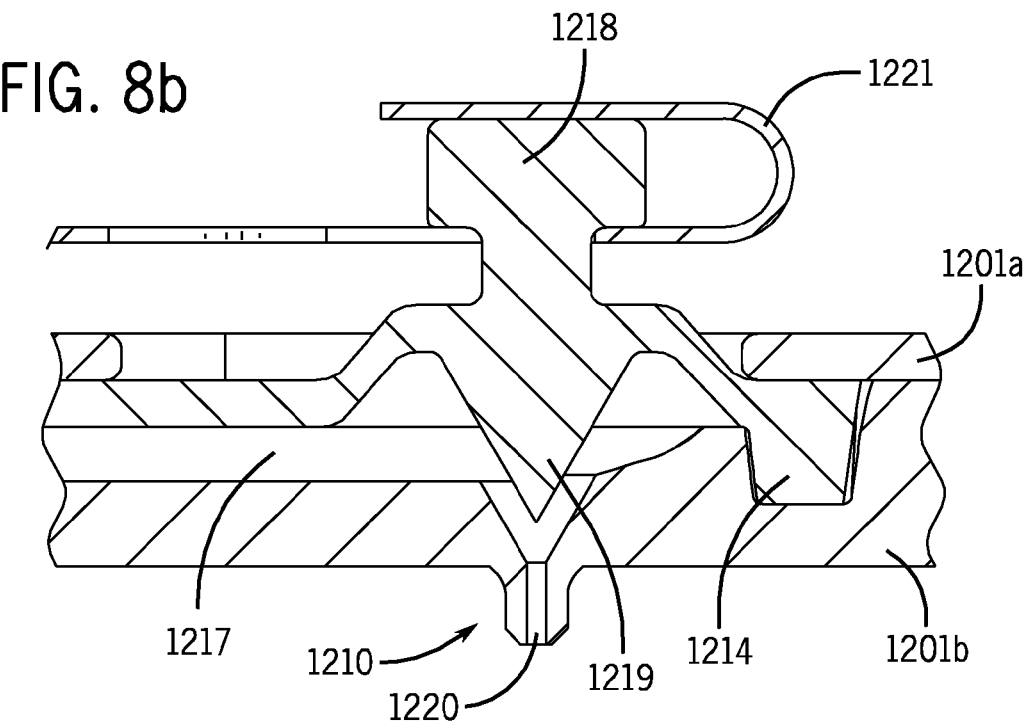
FIG. 8b is a cross-section view taken along line 8-8 of FIG. 7 depicting a valve portion of the cassette in an open position.

FIGS. 8*a* and 8*b* depict a cross section taken along line 8-8 of FIG. 7 showing the fluid transfer region 1210 of the primary fluid routing portion 1201. The fluid transfer region 1210 has a valve 1218 that comprises a silicone valve plug 1219, that may be integrally formed with the diaphragm 1214; a valve nozzle 1220, that may be formed into the base 1201*b* of the primary fluid routing portion 1201; and a leaf spring 1221 that connects to and exerts a force on the valve plug 1219 to keep the valve closed until activation is desired. As shown in FIG. 8*a*, the valve plug 1219 is in the closed position, and fluid is not allowed to pass through the valve, but fluid may flow in the fluid channel 1217 of the primary fluid routing portion 1201. As shown in FIG. 8*b*, the valve plug 1219 is in the open position, and fluid is allowed to pass through the valve nozzle 1220.

Figure 9:
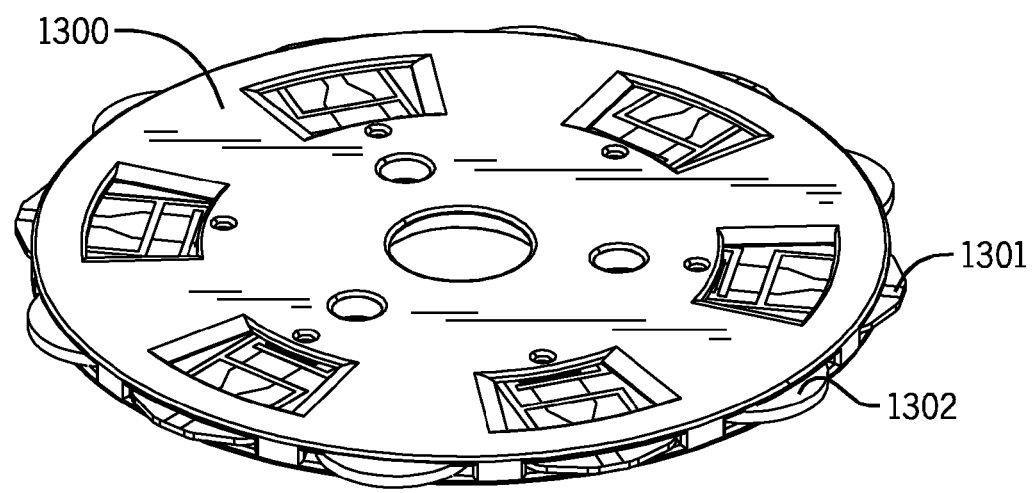
FIG. 9 is a pictorial view illustrating a disposable off-line testing disk for use with the testing system shown in FIG. 4.

In FIG. 9, the secondary fluid routing portion 1300, where secondary testing such as off-line testing can be done, is depicted. The secondary fluid routing portion 1300 has at least one test sensor 1301, which may be a single use or multiple use sensor. Optionally, an absorbent pad 1302 can be provided. The exemplary embodiment depicted in FIG. 9 shows that the secondary fluid routing portion 1300 can include a plurality of test sensors 1301 and a plurality of absorbent pads 1302. The test sensors 1301 shown are single use blood coagulation sensors. The coagulation test sensors 1301 may use a PT reagent, an aPTT reagent, or an ACT reagent. A sample of blood from the primary fluid routing portion 1201 is transferred through the fluid transfer region 1210 and onto the test sensor 1301 for off-line testing. It is contemplated that a sample as small as 5 µL, may be used for blood coagulation testing with a PT reagent. The test sensor 1301 can absorb a 5 µL, sample in about 5 seconds using capillary action. Electrodes (not shown) relay the results of the coagulation test to the system 1000.

Figure 10:
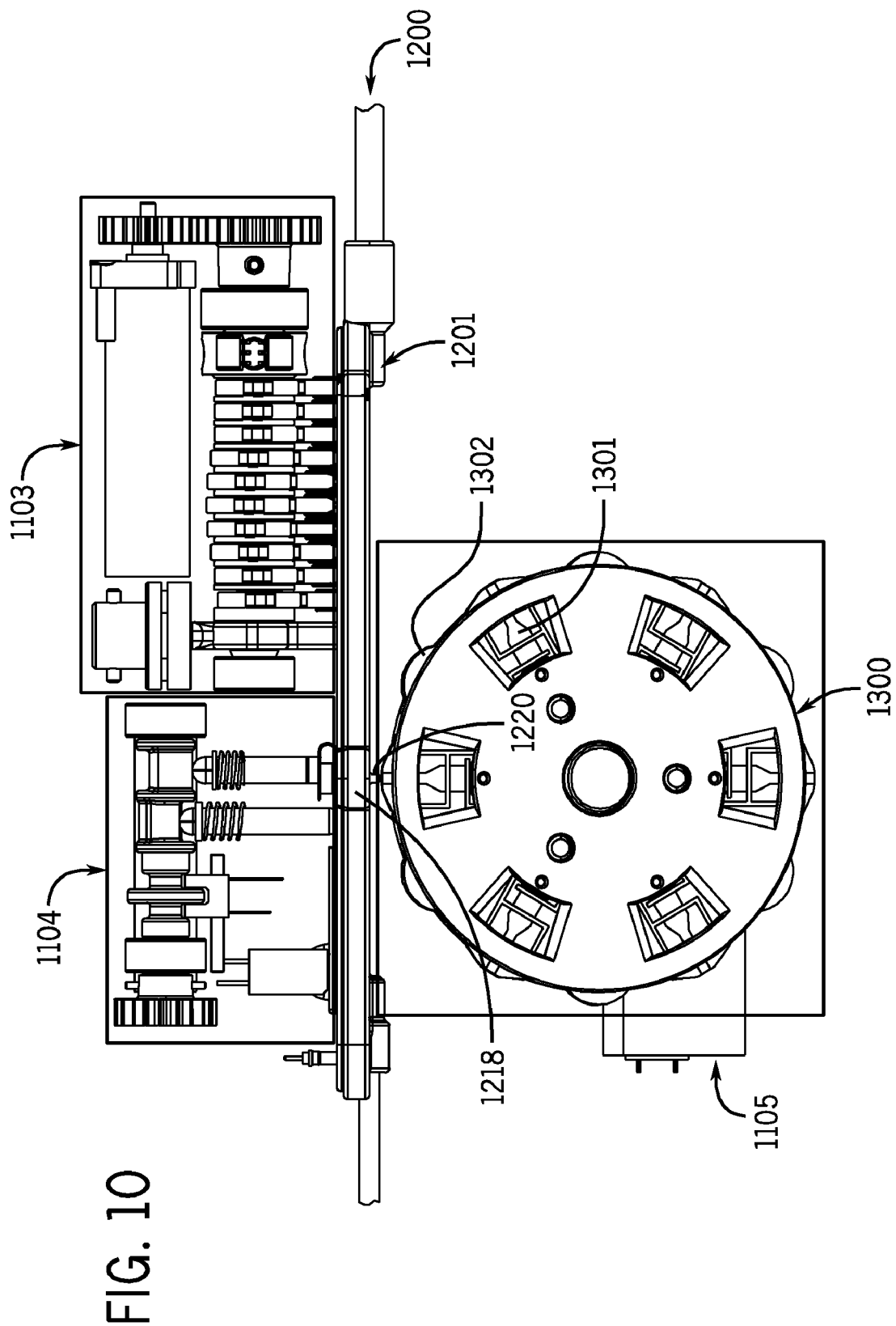
FIG. 10 is a pictorial view illustrating movable mechanisms of the testing system according to the embodiment of FIG. 4.

Turning now to FIG. 10, mechanisms for operating moving components of the system 1000 are shown. The system 1000 has a pump 1103, a valve actuator 1104, and an off-line testing portion sensor indexer 1105. The pump 1103 and the valve actuator work in conjunction with the primary fluid routing portion 1201 of the system 1000, while the off-line testing portion sensor indexer 1105 works in conjunction with the secondary fluid routing portion 1300.

Figure 11:
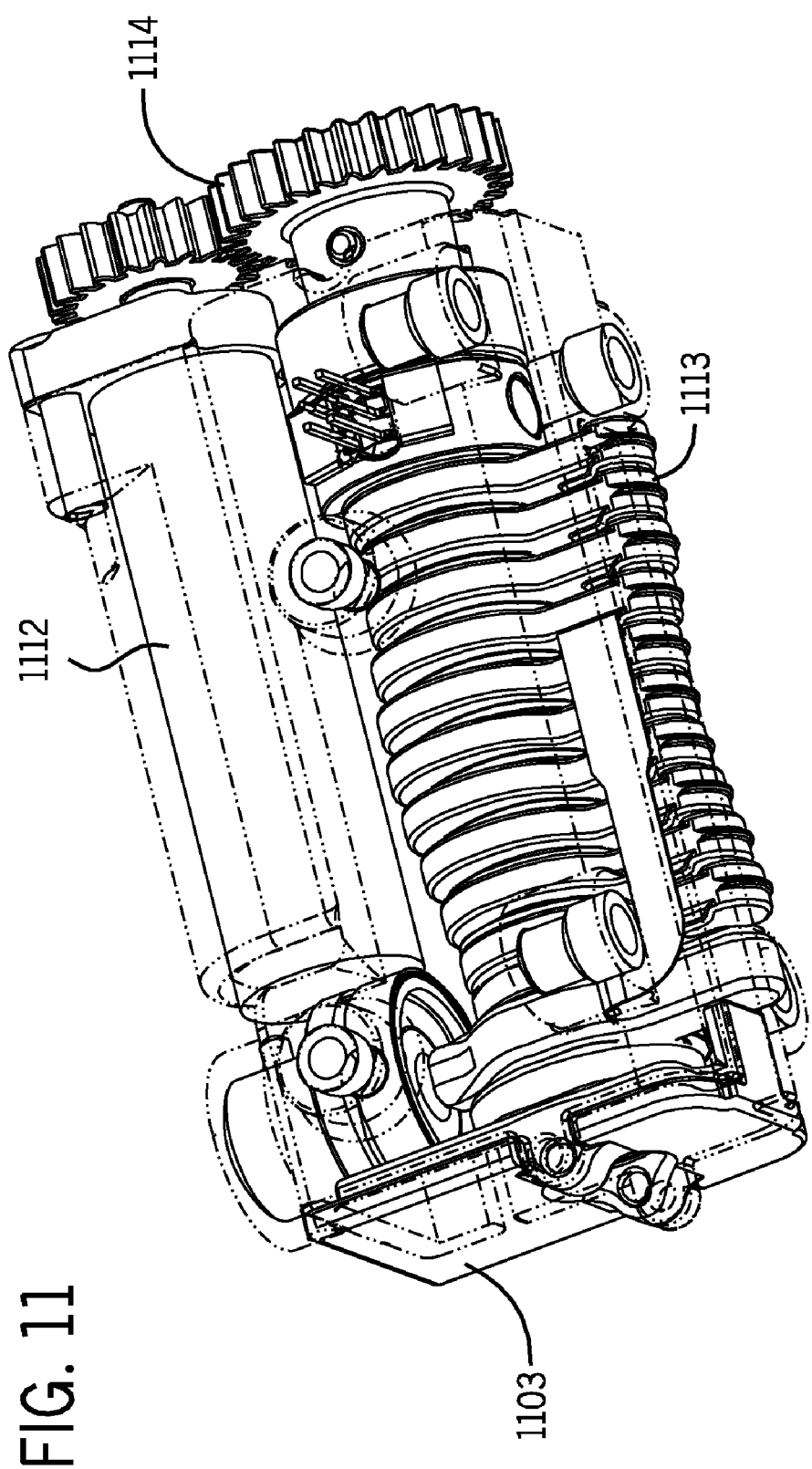
FIG. 11 is a pictorial view depicting a peristaltic pump mechanism for use with the testing system shown in FIG. 4.

The pump 1103 is shown in more detail in FIG. 11. The pump 1103 has a motor 1112, a peristaltic portion 1113 having peristaltic fingers mounted on a camshaft, and a set of gears 1114 to allow the motor 1112 to drive the peristaltic portion 1113. The motor 1112 is operable in either direction, thus allowing the pump to be operated to draw fluid into the primary fluid routing portion 1201, or to pump fluid out of the primary fluid routing portion 1201 or back in the direction from which it entered. Therefore, the pump 1103 provides for bidirectional flow within the system 1000.

Figure 12:
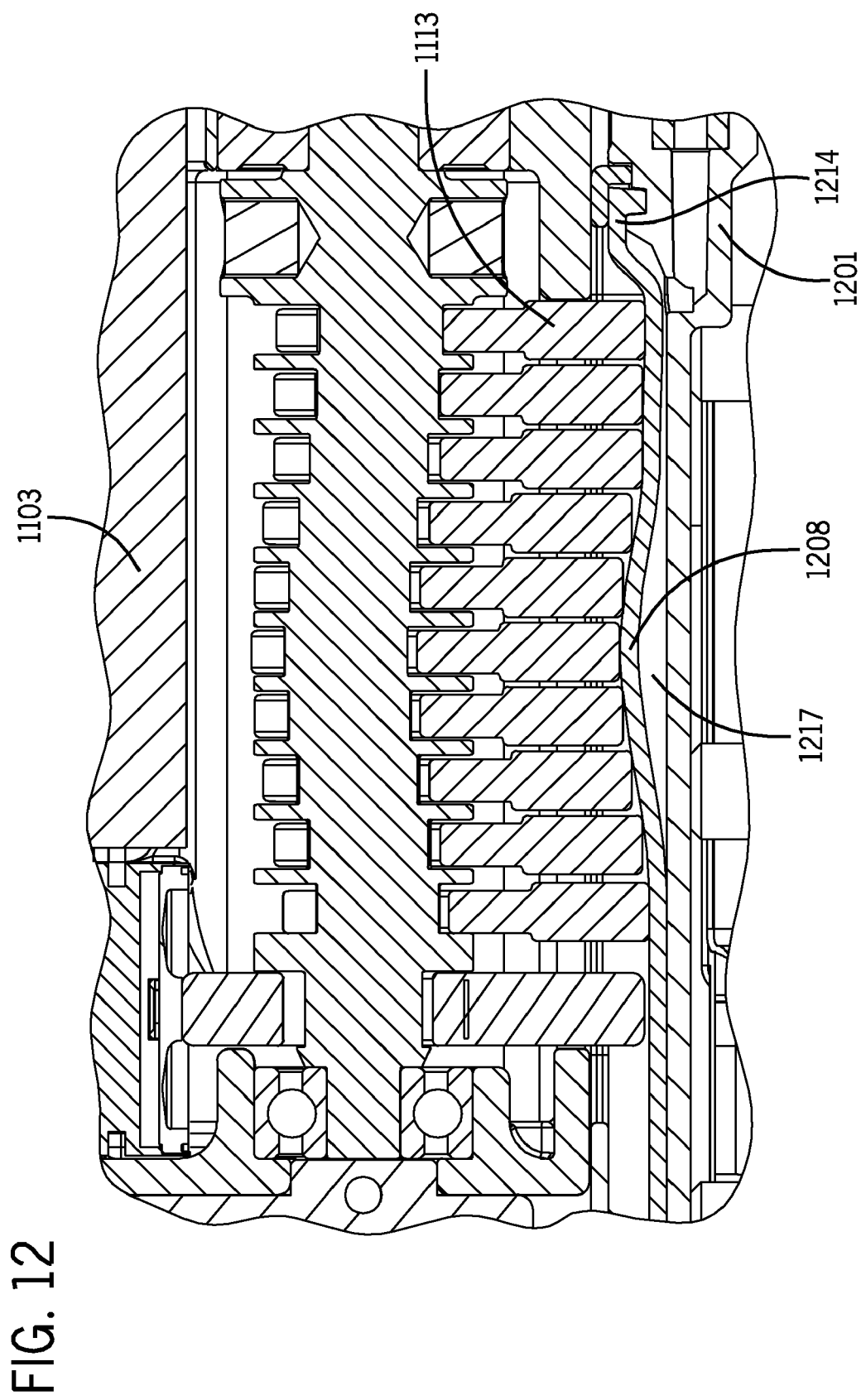
FIG. 12 is a cross-sectional view taken along line 12-12 of FIG. 10 depicting the peristaltic pump interacting with the cassette for pumping fluid into or out of the cassette.

FIG. 12 depicts a cross-section showing the pump 1103 interacting with the pump region 1208 of the primary fluid routing portion 1201. The peristaltic fingers of the peristaltic portion 1113 of the pump 1103 compress the silicone diaphragm 1214 in the pump region 1208 of the primary fluid routing portion 1201. The fingers sequentially press against the diaphragm 1214 to cause fluid to flow in flow channel 1217 of the primary fluid routing portion 1201 and the system 1000. As is well known in the peristaltic pump field, at least some of the fingers are positioned to compress the diaphragm 1214 sufficiently so that no fluid may flow through the flow channel 1217 when the pump 1103 is not in operation and the cassette 1201 is properly installed.

Figure 13:
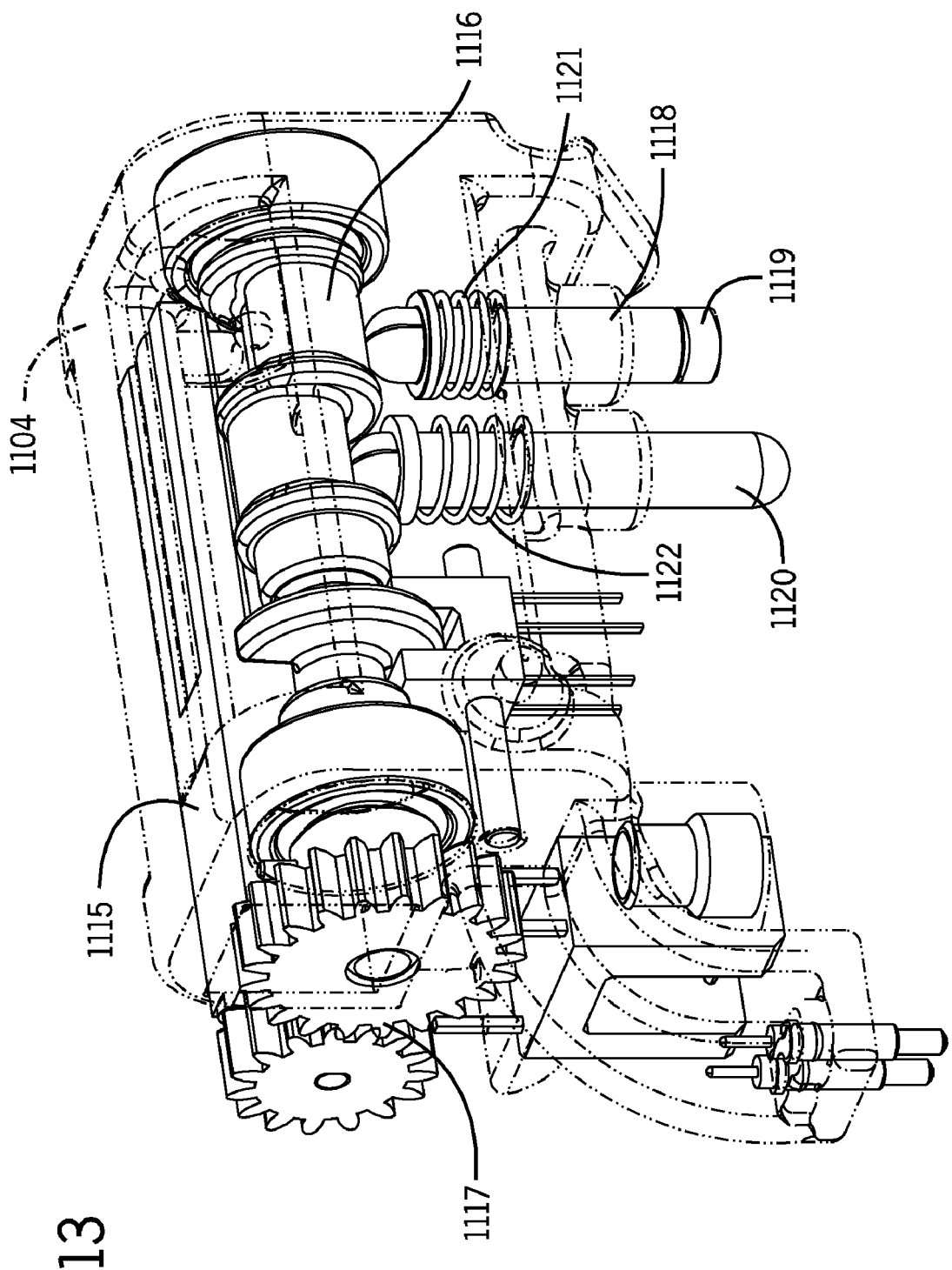
FIG. 13 is a pictorial view illustrating an actuator adapted to operate the valve of the cassette as shown in the embodiment of FIG. 7.
Figure 14A:
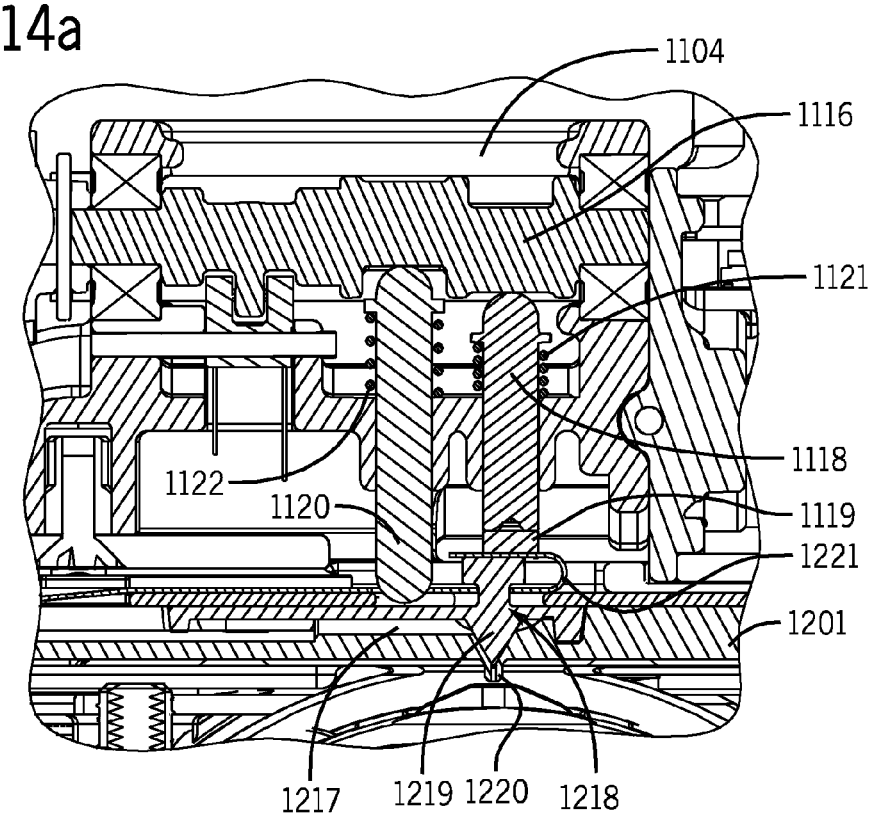
FIG. 14a is a cross-sectional view depicting the actuator depicted in FIG. 13 interacting with the cassette with the valve in a closed position.
Figure 14B:
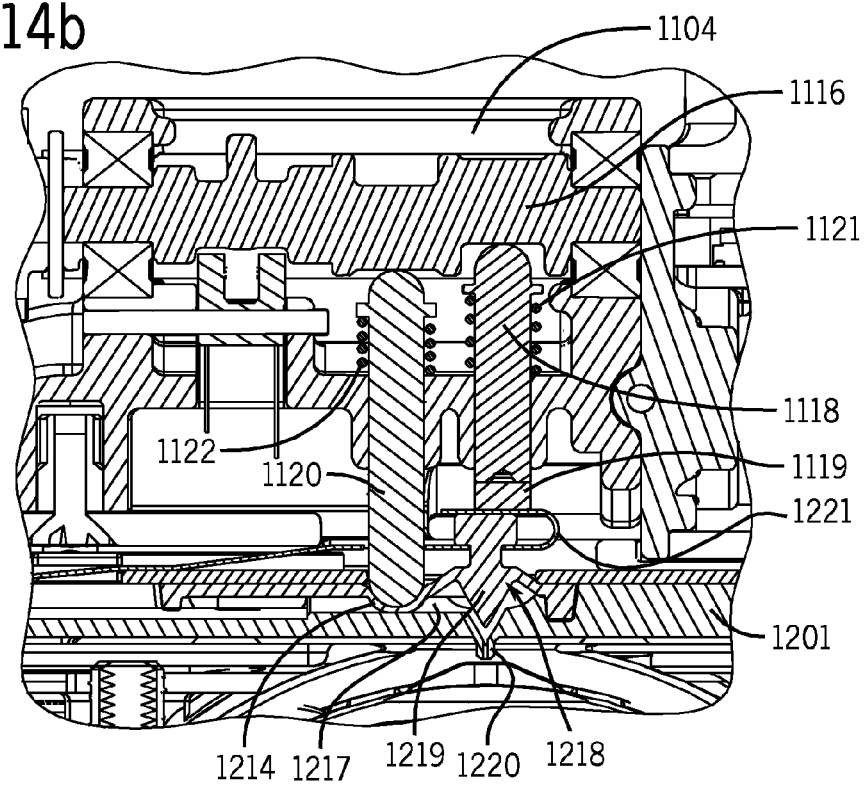
FIG. 14b is a cross-sectional view depicting the actuator depicted in FIG. 13 interacting with the cassette with the valve in an open position.

Next, FIGS. 13, 14*a*, and 14*b* show the valve actuator 1104 in more detail. The valve actuator 1104 has a motor 1115 that drives a camshaft 1116 via gears 1117. The cam shaft 1116 operates a valve pin 1118 and a diaphragm pin 1120. The valve pin 1118 has a spring 1121 and the diaphragm pin 1120 has a spring 1122 that hold the pins 1118, 1120 in contact with the camshaft 1116. The valve pin 1118 has a magnet 1119 on the end of the pin closest to the primary fluid routing portion or cassette. To open the valve 1218, as shown in FIG. 14*b*, the camshaft 1116 turns, allowing the spring 1121 to push the valve pin 1118 away from the primary fluid routing portion 1201. The magnet 1119 lifts up a leaf spring 1221 that is connected to the valve plug 1219, pulling the valve plug 1219 away from the valve nozzle 1220 to allow fluid to flow through the valve nozzle 1220. Simultaneously, the motion of the camshaft 1116 causes the diaphragm pin 1120 to move towards the primary fluid routing portion 1201. The diaphragm pin 1120 compresses the silicone diaphragm 1214 so that fluid may not be pumped distally beyond the location of the pin 1120 in the flow channel 1217 of the primary fluid routing portion 1201. When the valve plug 1219 is positioned to allow flow through the valve nozzle 1220, the pump 1103 may be run for a short period of time to more quickly drain fluid from the primary fluid routing portion 1201 to the secondary fluid routing portion 1300. Once the fluid has been transferred to the secondary fluid routing portion 1300, the camshaft 1116 rotates to push the valve pin 1118 back towards the primary fluid routing portion 1201, thus replacing the valve plug 1219. Simultaneously, the diaphragm pin 1120 is moved away from the primary fluid routing portion to allow flow to resume through the flow channel 1217, as shown in FIG. 14*a*. The period to open or close the valve 1218 is less than five seconds.

Figure 16:
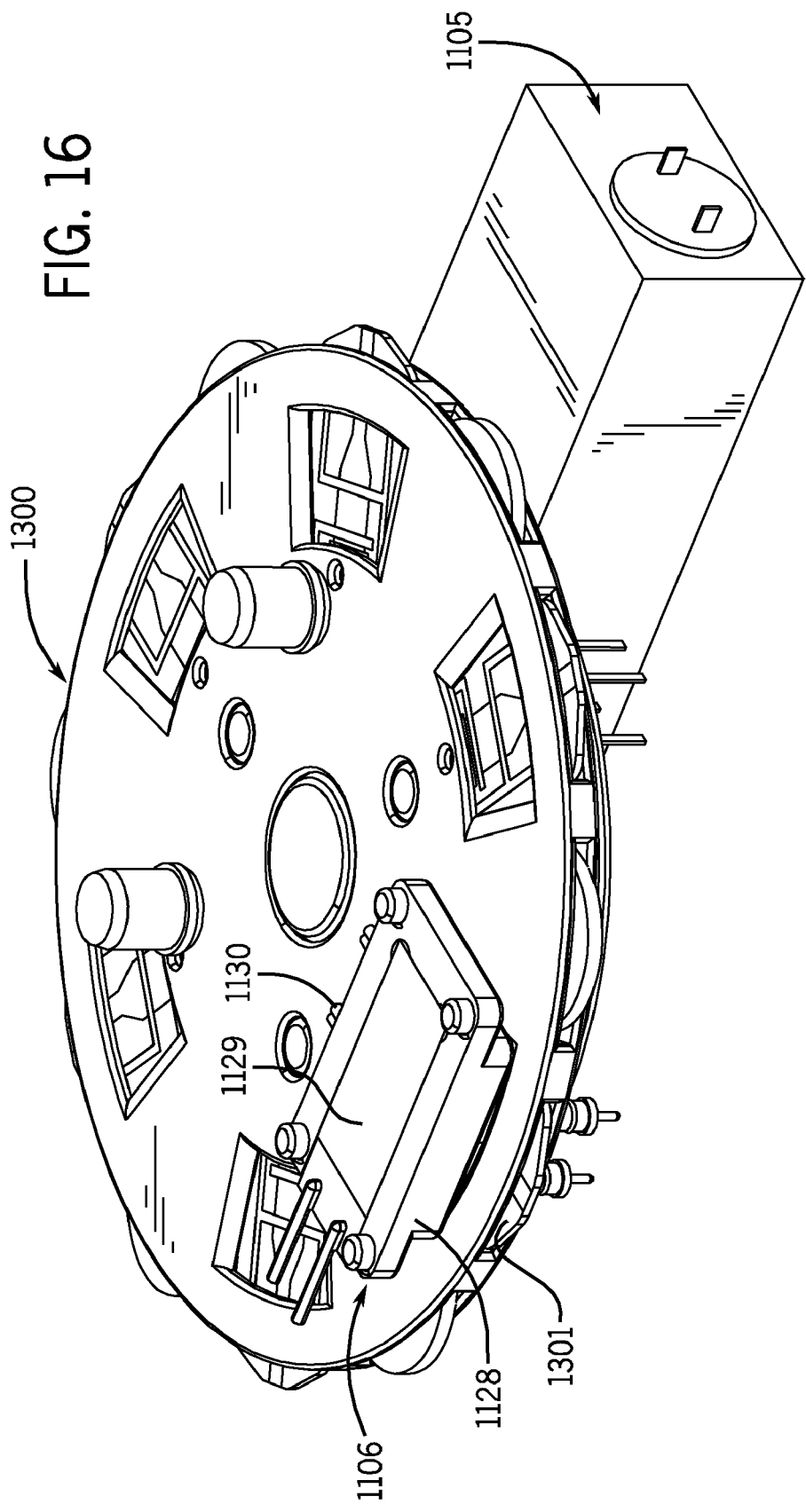
FIG. 16 is a top pictorial view of a rotating mechanism for the disposable off-line testing disk for use with the testing system shown in FIG. 4.

Referring now to FIGS. 15 and 16, the off-line sensor portion indexer 1105 is depicted. The sensor indexer 1105 has a carousel 1123 that supports the off-line testing portion 1300 to properly position the off-line test sensors 1301 and the absorbent pads 1302. The sensor indexer 1105 drives the carousel 1123 via geared surface 1124. The rotational position of the carousel 1123 is sensed by monitoring movement of flags 1125 through an optical detector 1126. A set of pins 1127 contact electrodes on the off-line test sensors 1301 to obtain results from the off-line test sensors. Also shown is a heater 1106 used to maintain an appropriate temperature of the off-line test sensor 1301 being used. The heater has an aluminum element 1128 that contact the sensor 1301 to transfer heat to the sensor 1301. The element 1128 is heated by a Kapton pad 1129 that is electrically energized. A thermistor 1130 embedded in the element 1128 monitors the temperature. The heater 1106 is mounted in a fixed location, and an individual sensor 1301 is rotated to the heater 1106 by the carousel 1123. Alternatively, each sensor 1301 may include a heater 1106 that rotates with it or the heater 1106 can be on a second carousel geared to rotate relative to the sensor carousel 1123.

Referring again to FIG. 1, a method of using the point-of-care testing system 10 on a patient may comprise attaching the main body 100 to the patient's forearm to monitor blood glucose level and coagulation (aPTT) rate at prescribed intervals of time over a twenty-four hour period. An infusion system or pump 400 near the patient has been configured to function as the graphical user interface 401 for the system 10 via wired or wireless communication. The infusion pump 10 may also serve to deliver one or more drugs to the patient, such as insulin and heparin.

A caregiver or clinician gathers the basic components of the system in preparation for use on the patient, including the main body 100, the disposable portion 200 (including the primary fluid routing portion 201 and/or the secondary fluid routing portion 300), and the reservoir of flush solution 207. The clinician also obtains a standard catheter 205 suitable for drawing blood from a peripheral vein on the patient's forearm. The disposable 200 portion incorporates a glucose sensor in the diagnostic sensor region 209, and the disposable secondary fluid routing portion 300 incorporates an array of six aPTT coagulation sensors.

The clinician attaches the body 100 to the patient via the attachment features 101, such that the body 100 is located about three inches from a site chosen to catheterize a peripheral vein or artery. In the embodiment shown, the forearm provides a convenient location for mounting the body 100 to the patient and accessing a peripheral blood vessel, although other mounting locations and blood vessel access points are possible.

The clinician then assembles the disposable portions 200, 300 of the system, by connecting the distal connector 204 to the catheter 205, connecting the secondary fluid routing portion 300 to the primary fluid routing portion 201, and connecting the proximal connector to the flush solution 207 reservoir.

The clinician primes all the fluid passages in the system 10 with flush solution by holding the flush solution reservoir 207 at an elevation that causes gravity to force the flush solution through all passages from the reservoir 207 to the tip of the catheter 205. The clinician observes that all air has been removed from these passages.

The clinician inserts the catheter 205 into the peripheral vein or artery on the patient, using appropriate hospital procedures, to provide access to the patient's blood vessel.

The clinician immediately installs the primary fluid routing portion 201 and the secondary fluid routing portion 300 into the main body 100 via the opening 102 (FIG. 3). When the opening g102 is closed by the door 111, the installation automatically prevents the flow of flush solution inside the primary fluid routing portion 201, by virtue of the pump 103 engaging the primary fluid routing portion 201. The clinician then hangs the flush solution reservoir 207 on a bedside pole.

The clinician activates ("turns on") the invention via the graphical interface 401 on the infusion pump 400. The system 10 is subsequently energized by the internal power source 108. Wireless communication between the main body and the infuser 400 begins, via a set of wireless transmission components on the electronic controller 107 and in the infuser 400.

The clinician programs the system 10 via the graphical interface 401 to perform a series of 24 blood draws on the patient, spaced 1 hour apart. Furthermore, the clinician programs the invention to perform a glucose test on each blood sample drawn, and also to perform an aPTT test on every second blood sample drawn (i.e., at 2-hour intervals). The net result will be 24 glucose tests and 12 aPTT tests uniformly spaced over a 24-hour period.

The system 10 begins to respond to the instructions programmed by the clinician. All acts done by the system 10 to perform successive cycles of drawing, testing, and re-infusing the blood sample are coordinated by the electronic controller 107 using power from the power source 108.

The sensor indexer 105 is briefly activated to prepare one of six aPTT sensors 301 to receive a blood sample from the fluid transfer region 210 and to receive heat from the heating element 106.

The heating element 106 is activated, causing the aPTT sensor in to reach a temperature of 37° C. within about 30 seconds.

The pump 103 is activated for about 20 seconds, causing the cassette pumping region 208 to draw about 1 mL of blood from the patient through the catheter 205 into the disposable portion 200, reaching a maximum point somewhere in the proximal tubing 203. The incoming blood displaces and partially mixes with the flush solution in the disposable portion 200; however, sufficient flush solution is displaced from the sensor region 209 and the transfer region 210 to permit accurate diagnostic measurements on the blood sample.

The pump 103 is deactivated upon completion of the draw, preventing any further flow of blood or flush solution in the system 10.

The glucose sensor in the sensor region 209 is activated to begin a measurement of glucose concentration in the blood sample.

The fluid transfer mechanism 104 is briefly activated, causing the fluid transfer region 210 to transfer a 10 μL volume of blood sample to the aPTT sensor 301. The transfer is assisted by a brief activation of the pump 103 to exert fluid pressure on the 10 μL blood sample until it completely fills the off-line test sensor 301. This transfer process takes about 5 seconds to complete.

The aPTT sensor 301 is activated to begin an aPTT measurement on the blood sample. The heating element 106 continues to operate to maintain the sensor 301 and blood sample at a temperature of 37° C.

The glucose sensor in the sensor region 209 completes the measurement of glucose concentration in the blood sample after about 20 seconds of test time. The result is read electronically by the electronic controller 107 which wirelessly transmits the result to the graphical interface 401 for the clinician to observe.

The pump 103 is activated for about 60 seconds, causing the pumping region 208 to re-infuse the blood sample in the disposable in-line portion 200 back to the patient via the catheter 205. Virtually all of the 1 mL of drawn blood is re-infused, excluding the 10 μL sample transferred to the aPTT sensor 301. This pumping process also causes about 1 mL of flush solution 207 to be infused into the patient, which helps to cleanse the fluid passages in the system 10 and the catheter 205 from any residual blood that may impair the operation of the system 10.

The pump 103 is deactivated upon completion of the re-infusion step, preventing any further flow of flush solution in the system 10.

The aPTT sensor 301 completes the measurement of aPTT in the blood sample after about 120 seconds of test time. The result is read electronically by the electronic controller 107 which wirelessly transmits the result to the graphical interface 401 for the clinician to observe.

The heating element 106 is deactivated, causing its temperature level to equilibrate with the surrounding ambient temperature within a few minutes.

The system 10 remains idle for nearly 1 hour in preparation for the next programmed blood draw and test cycle. The total cycle time to perform the blood draw, glucose test (with blood transfer step), and re-infusion step is about 100 seconds.

At programmable predetermined intervals, by way of example and not limitation approximately hourly, the system automatically repeats the above tests as programmed. However, all steps involving the aPTT test can be performed according to the same or a different programmable schedule, for example an aPTT test may be performed only for every second cycle per the clinician's instructions.

Once all six aPTT sensors 301 have been consumed during operation of the system 10 (i.e., after 11 cycles of operation), the electronic controller 107 wirelessly instructs the infuser 400 and graphical display 401 to notify the clinician. The clinical responds by detaching the secondary fluid routing portion 300 from the main body 100 via the access door 111, and replaces it with a fresh secondary fluid routing portion 300. The clinician or caregiver then discards the consumed secondary fluid routing portion 300 per hospital procedures.

Upon completion of use of the system 10 on the patient for the desired number of cycles of operation, the clinician disconnects the system from the patient. The clinician removes the catheter 205 from the patient according to hospital procedure, and removes the main body 100 from the forearm via the attachment features 101. The clinician then removes the testing portions 201, 300 from the main body 100 via the access door 111. The clinician discards the catheter 205, testing portions 201, 300 and the flush solution container 207 per hospital procedures.

As described with respect to the glucose/coagulation sampling and test examples above, the in-line sensors and the off-line sensors can measure a different characteristic of the fluid sample. Alternatively, the in-line sensors and the off-line sensors can measure the same fluid sample characteristic. In one example, both the in-line and off-line sensors can measure glucose. A single use off-line strip, such as is known in the art, can be used periodically (daily, hourly, or before, during or after selected cycles of in-line testing) to calibrate or mathematically correct for any drift in an in-line glucose sensor. If the in-line sensor was more stable and accurate than the off-line sensor, the in-line sensor could be used to calibrate or adjust readings from the off-line sensor. Such ability to cross calibrate the sensors is advantageous. In the case of calibrating the in-line sensor with the off-line sensor, it could even eliminate the need for the flush solution to have calibration traits, reducing costs and potential risks of adverse reactions with the flush solution. In any event, the need for other blood draws to check the accuracy of the sampling system 10 would be reduced.

It is further contemplated that the either of the in-line sensors or off-line sensors can include multiple sensors for sensing the same or different characteristics of the fluid sample. For example, the in-line sensor may include multiple sensors—all for glucose or one for glucose, one for lactate, etc. The in-line sensors may be similar or of different types. Likewise for example, the off-line sensor may include multiple sensors—all for coagulation or one for coagulation, one for glucose, etc. The off-line sensors may be similar or of different types. Multiple off-line sensory arrays can be operatively brought into position to receive a fluid sample through the valve. A single expression of a fluid sample can be routed to multiple off-line sensors through capillary action or other known methods.

One of the advantages of the invention is the capability to program and selectively run an in-line test, an off-line test or both according to the condition of the patient and the desire of the clinician. The sampling interval can be preset, but also can be dynamically adjusted or tailored based upon the results obtained or clinician preferences. For example, the system 10 can be programmed to measure both coagulation and glucose every thirty minutes during the initial few hours a patient is in an intensive care unit following surgery. Then, the expression of samples for coagulation testing can be reduced in frequency if the clinician desires or the sample readings are as expected or desired. If an unexpected reading is encountered, the frequency can be increased or the appropriate in-line and/or off-line test or re-test automatically initiated. To minimize the number and volume of blood draws from patients, the system 10 can selectively run only one of the sensors at a time if desired. For example, if the in-line sensor gives an unexpected reading, it is possible to selectively repeat testing only with that sensor. This has the beneficial result of minimizing the number of expressions (opening of the valve or fluid transfer region) for off-line testing since each expression results in a brief, controlled breach of the sterile field.

It is contemplated that the system 10 can include a fill port at the fluid transfer region 210, between the pump 103 and the fluid source 207, or between the pump 103 and the catheter 205. The fill port is used for drawing blood, manually or more preferably automatically, into a test tube or other suitable known container for subsequent analysis at a remote laboratory or analyzer. The fill port can be provided on a Y site connected to the primary fluid routing portion 200. The pump 103 can be programmed to draw blood into the test sample container on demand or at static predetermined or dynamic intervals for more complete blood panels. The patient is freed from more frequent sticks with needles, which also reduces the risk of needle sticks for clinicians and reduces hazardous waste.

Figure 17:
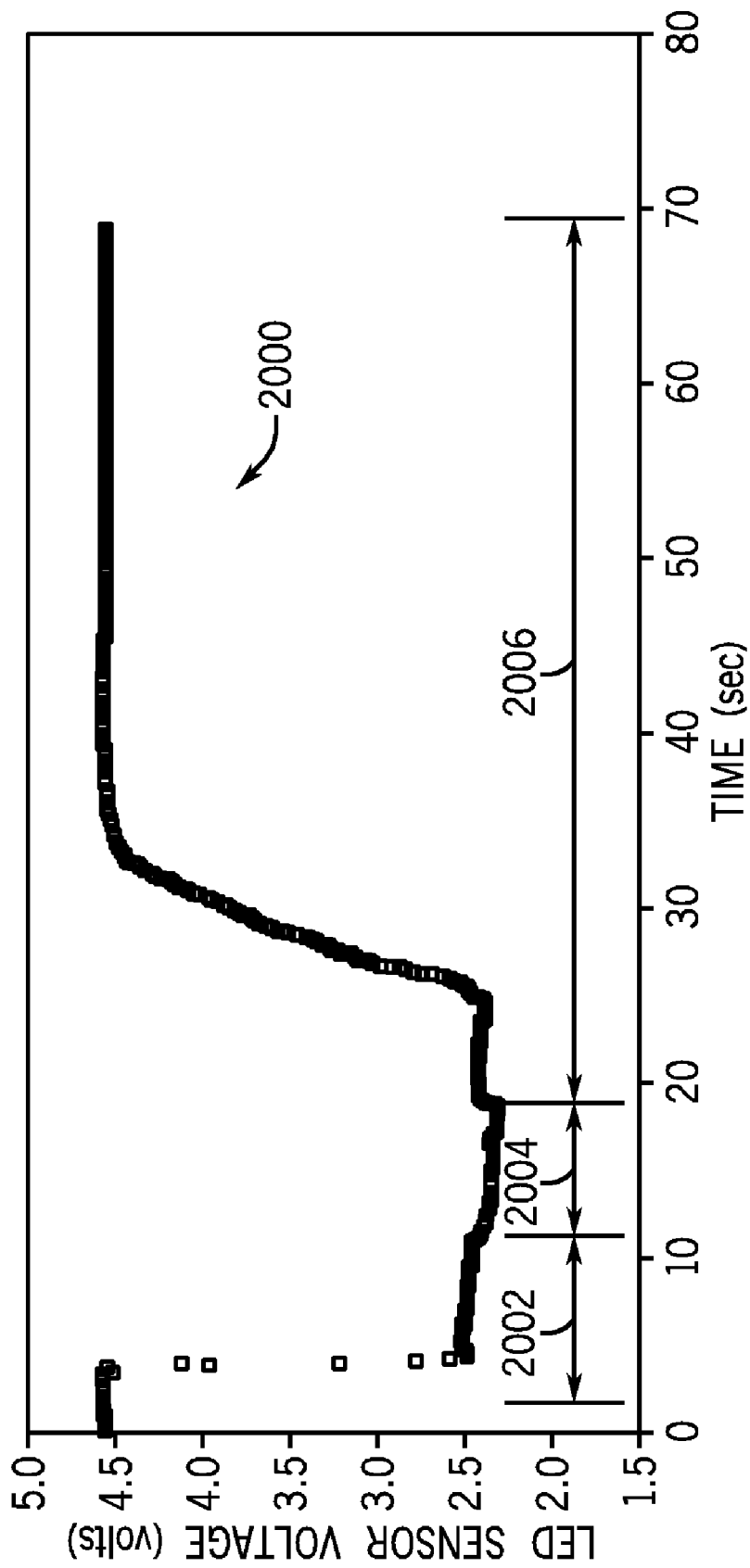
FIG. 17 is a graph showing the output voltage versus time for an optical sensor for use with the testing system.

Turning now to FIG. 17, a plot of voltage versus time for the optical sensor 1227 as blood is drawn into the disposable portion 1200 of the system 1000 over the course of one draw and flush cycle 2000 during normal operation. As blood is drawn into the system 1000, the voltage output of the sensor 1227 decreases, as less light passes through blood than passes through flush solution. The draw and flush cycle 2000 depicted in FIG. 17 includes a draw portion 2002, where fluid is pumped at a rate of 3.0 mL/min into the system 1000. A target volume of 0.5 mL is drawn into the system during the draw portion 2002. Output of the optical sensor 1227 is sampled at a rate of 10 outputs per second during the draw and flush cycle 2000. Once blood enters into the disposable portion 1200, during the draw portion 2002, the voltage output of the optical sensor 1227 rapidly decreases from about 4.5 volts to about 2.5 volts.

The draw portion 2002 begins about 1.4 seconds after data collection is initiated and lasts until about 11.4 seconds after data collection is initiated, thus lasting about 10 seconds.

A pause portion 2004 of the draw and flush cycle 2000 lasts from about five to ten seconds, more specifically from about six to nine seconds, and even more specifically from about seven to eight seconds. The pause portion 2004 is typically when testing of the fluid within the disposable portion 1200 of the system 1000 occurs.

Following the pause portion 2004, a flush portion 2006 of the draw and flush cycle 2000 occurs. Fluid is pumped at a rate of 3.0 mL/min from the system 1000 during the flush portion 2006. A target volume of 2.5 mL is flushed from the system 1000 during the flush portion 2006. The 2.5 mL flushed from the system 1000 during the flush portion 2006 includes the 0.5 mL of blood drawn into the system 1000 during the draw portion 2002, as well as about 2 mL of flush solution.

Output voltage of the optical sensor 1227 gradually increases during the flush portion 2006 from about 2.5 volts to about 4.5 volts. The increase in voltage during the flush portion 2006 is generally more gradually than the decrease in voltage during the draw portion 2002.

The flush portion 2006 begins at about 19 seconds after data collection is initiated from the optical sensor 1227 in FIG. 17, and terminates at about 69 seconds after data collection is initiated. Thus, the flush portion 2006 lasts for about 50 seconds.

Figure 18:
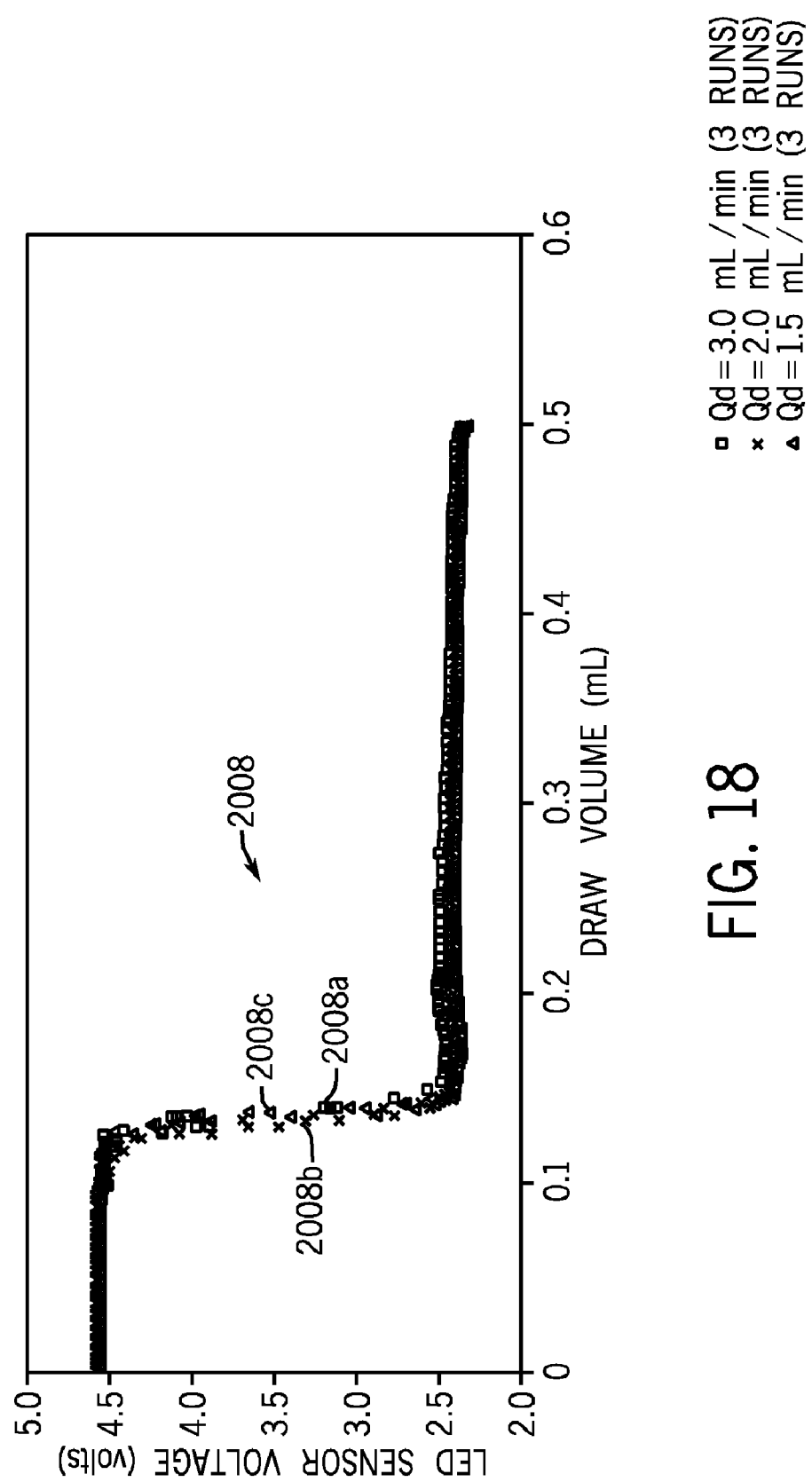
FIG. 18 is a graph showing the output voltage versus volume drawn for an optical sensor for use with the testing system.

FIG. 18 shows graphs of output voltage 2008a-2008c of the optical sensor 1227 plotted against draw volume during a draw portion for three different fluid flow rates. The first draw portion 2008a has a fluid flow rate of 3 mL/min, the second draw portion 2008b has a fluid flow rate of 2 mL/min, while the third draw portion 2008c has a fluid flow rate of 1.5 mL/min. As shown in FIG. 18, the output voltage of the optical sensor 1227 is generally similar for the three flow rates 2008a-2008c.

Figure 19:
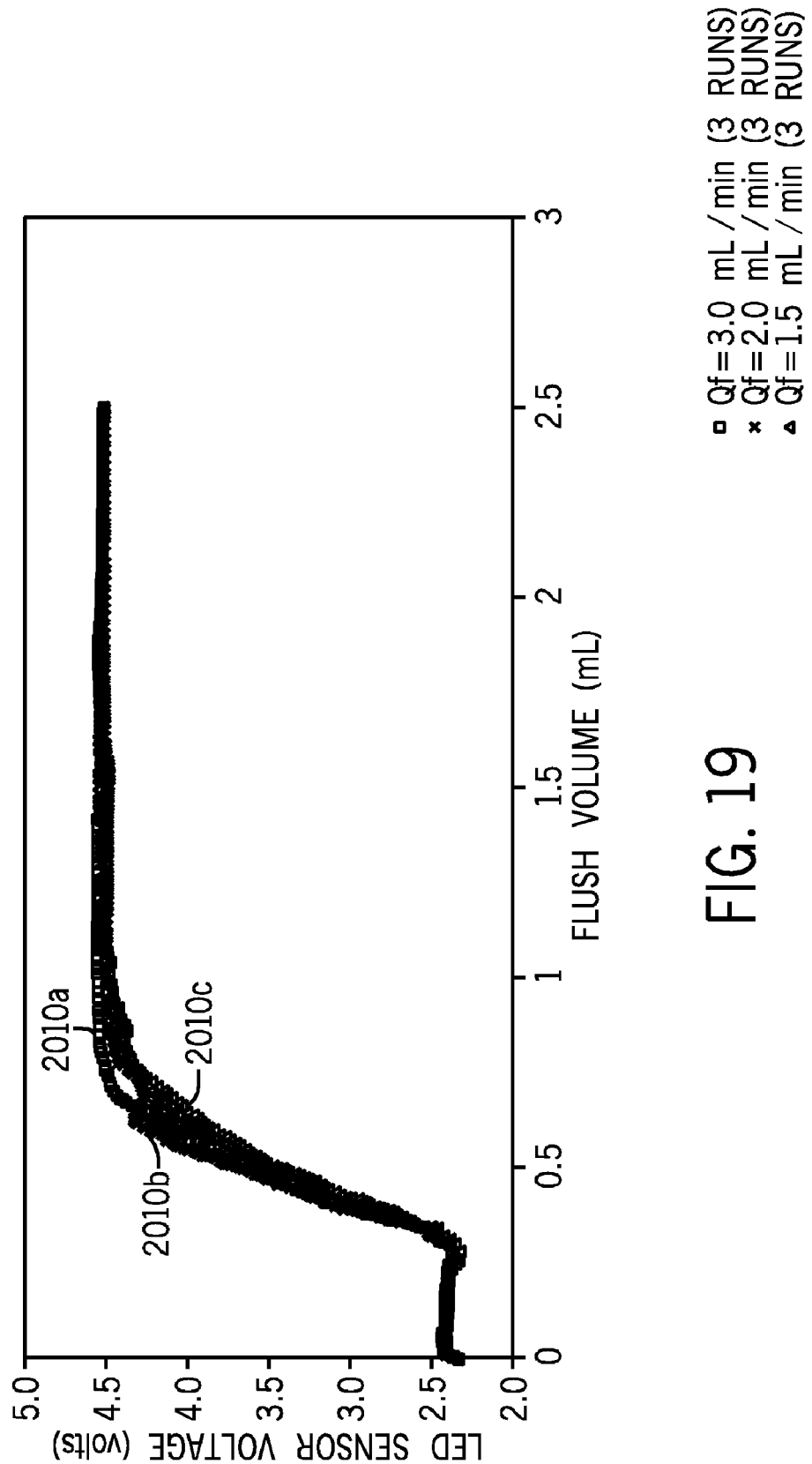
FIG. 19 is a graph showing the output voltage versus volume flushed for an optical sensor for use with the testing system.

Similarly, FIG. 19 shows graphs of output voltage 2010a-2010c of the optical sensor 1227 plotted against flush volume during a flush portion for three different fluid flow rates. The first flush portion 2010a has a fluid flow rate of about 3 mL/min, the second flush portion 2010b has a fluid flow rate of about 2 mL/min, and the third flush portion 2010c has a fluid flow rate of about 1.5 mL/min. FIG. 19 shows that a slight variation exists in the output voltage based upon the fluid flow rate, but that the output voltage shown for the three flow rates for the flush portions 2010a-2010c generally have a similar shape.

Figure 20:
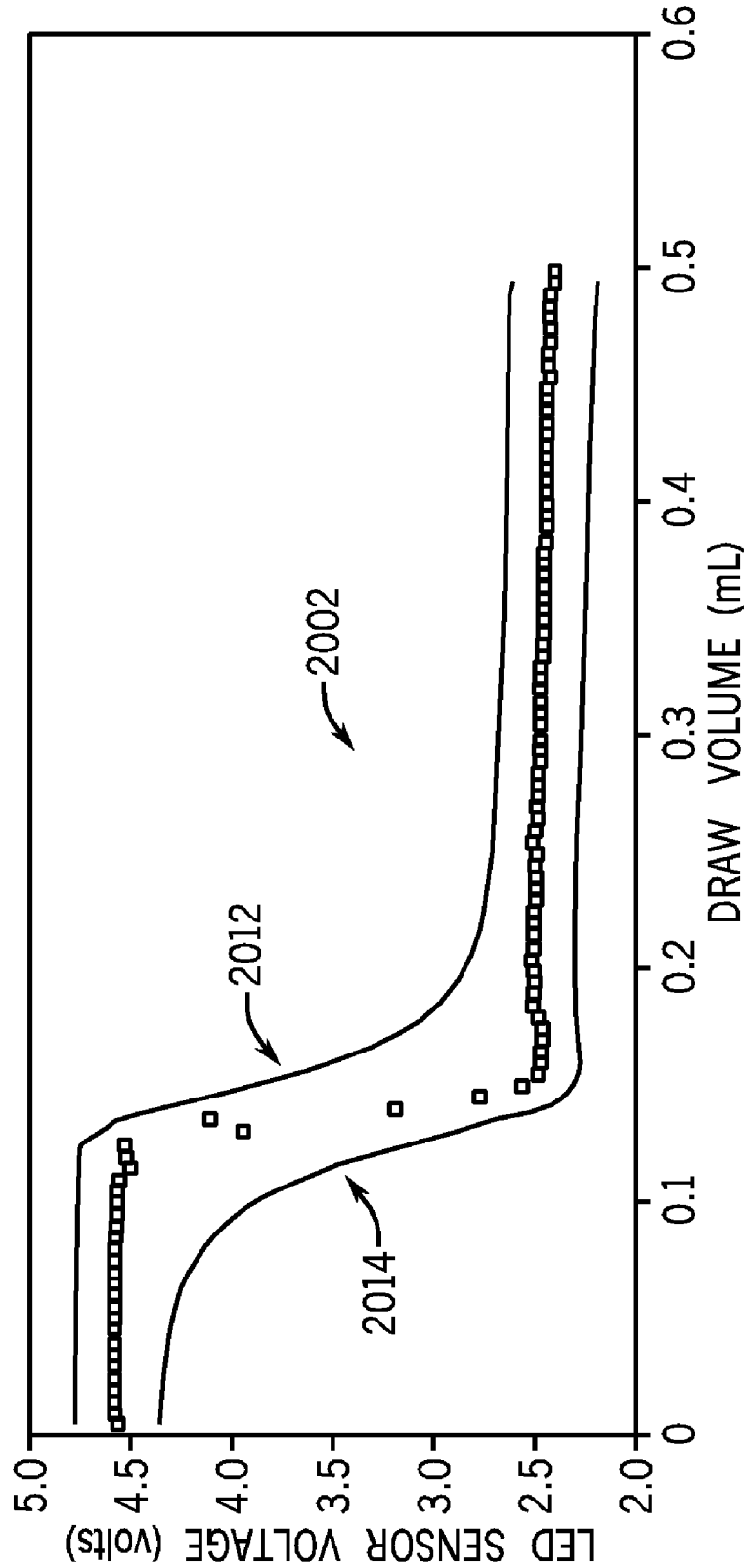
FIG. 20 is a graph showing the output voltage versus volume drawn for an optical sensor for use with the testing system also showing voltage limits.

Thus, as may be seen from FIGS. 18 and 19, the general shape of the graph of output voltage of the optical sensor 1227 does not vary greatly with flow rate, at least near anticipated operating flow rates of the system 1000. Therefore, it is possible to calculate upper acceptance limits and lower acceptance limits for the output of the optical sensor 1227 for the draw and flush cycle 2000. As shown in FIG. 20, an upper voltage limit 2012 and a lower voltage limit 2014 for the draw portion 2002 of the draw and flush cycle 2000. The upper voltage limit 2012 for the draw portion 2002 is a forward exponential moving average of the output voltage of the optical sensor 1227 with a positive offset value.

The upper voltage limit 2012 may be calculated utilizing the following formula:

$$ULD_i = ULD_{i-1} * (1-W_d) + (Xd_i + Sd) * Wd.$$

Conversely, the lower voltage limit 2014 for the draw portion 2002 is a reverse exponential moving average of the output voltage of the optical sensor 1227 with a negative offset value.

The lower voltage limit 2014 may be calculated using the following formula:

$$LLD_i = LLD_{i+1} * (1-W_d) + (Xd_i - Sd) * Wd.$$

The following variables are used to calculate the upper voltage limit 2012 and the lower voltage limit 2014.
$ULD_i$=the draw cycle upper acceptance limit at data point "i" (volts).
$ULD_{i-1}$=the draw cycle upper acceptance limit at the previous data point "i-1" (volts).
$ULD_1$=the draw cycle upper acceptance limit at the first data point (volts), $ULD_1 = Xd_1 + Sd$.
$LLD_i$=the draw cycle lower acceptance limit at data point "i" (volts).
$LLD_{i+1}$=the draw cycle lower acceptance limit at the next data point "i+1" (volts).
$LLD_n$=the draw cycle lower acceptance limit at the final data point (volts), $LLD_n = Xd_n - Sd$.
$Xd_i$=the LED sensor voltage for the draw cycle at data point "i" (volts).
$Xd_1$=the LED sensor voltage for the draw cycle at the first data point (volts).
$Xd_n$=the LED sensor voltage for the draw cycle at the final data point (volts).
$Vd_i$=the calculated draw volume at data point "i" (mL), $Vd_i = (Qd/60) * (td_i - td_1)$
$Vd_n$=the calculated total draw volume (mL), $Vd_n = (Qd/60) * (td_n - td_1)$.
Qd=the applied draw speed (mL/min).
$td_1$=the start time for the draw cycle, i.e., when the pump begins running (sec).
$td_n$=the stop time for the draw cycle, i.e., when the pump stops running (sec).
Sd=the user specified offset value for the draw cycle (volts), Sd>0.
Fd=the user specified fraction of the system dead volume for the draw cycle, Fd>0.
Wd=the calculated weighting factor for the draw cycle, Wd=2/(Nd+1).
Nd=the calculated number of moving data points for the draw cycle, Nd=Fd*DV/ΔVd.
DV=the sampling system dead volume (mL).

ΔVd=the incremental draw volume between successive data points (mL), ΔVd=Vd$_n$/(n−1)
n=the total number of data points comprising the draw cycle.

Thus, the equations above for the upper voltage limit 2012 and the lower voltage limit 2014 for the draw portion 2002 are a function of calculated volume drawn that may be stored into a memory accessible by a processor.

The user specified offset value Sd for the draw portion 2002 and the user specified fraction of the system dead volume Fd for the draw portion 2002 may be set depending on a particular test being performed, or the sensitivity required for testing a particular patient. Default values for the specified offset Sd and the dead volume Fd may be stored within the memory, but a caregiver may modify these values such that fewer error conditions are detected, thus reducing false positive error conditions.

Figure 21:
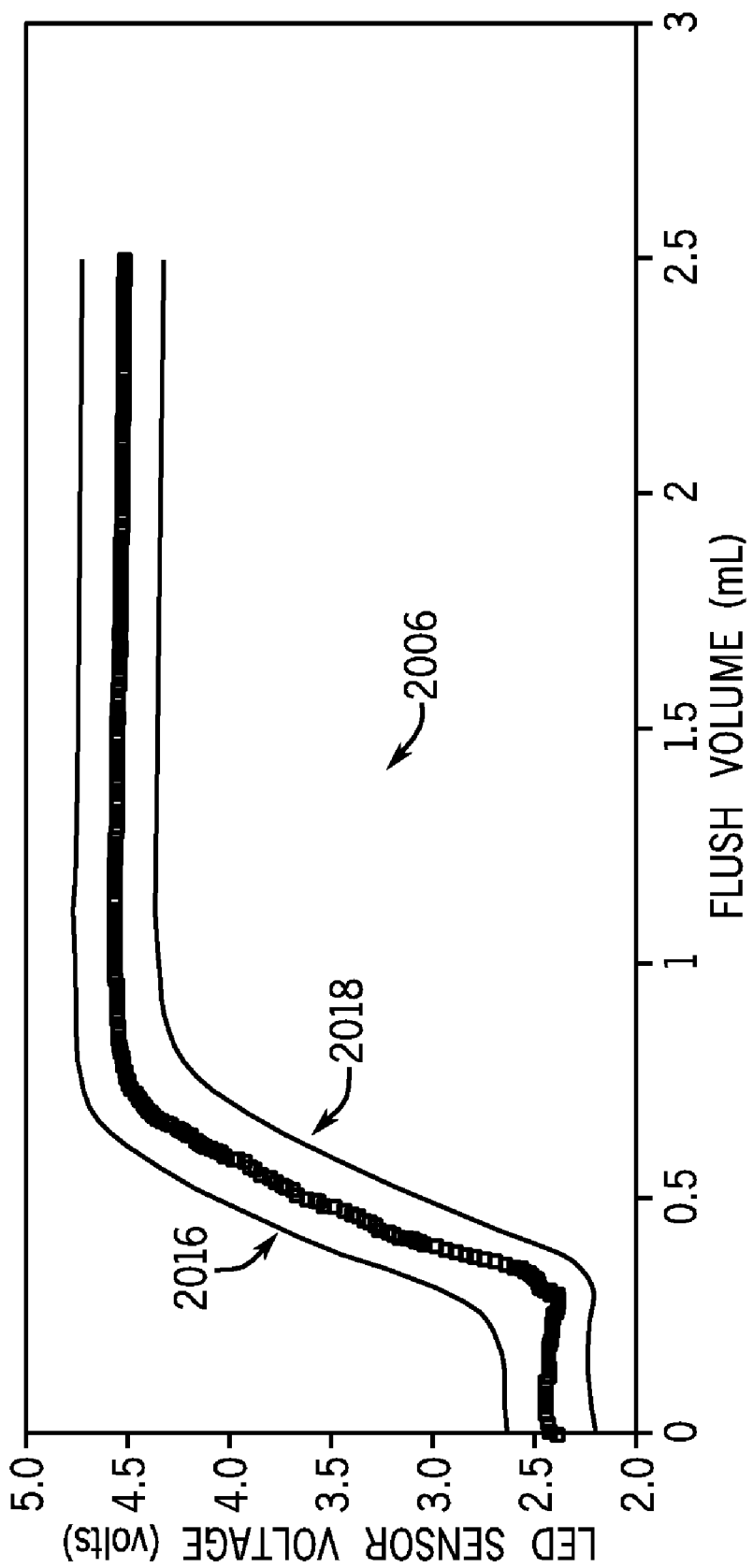
FIG. 21 is a graph showing the output voltage versus volume flushed for an optical sensor for use with the testing system also showing voltage limits.

Turning now to FIG. 21, an upper voltage limit 2016 and a lower voltage limit 2018 for the optical sensor 1227 during the flush portion 2006 of the draw and flush cycle 2000 is shown. The upper and lower voltage limits 2016, 2018 for the flush portion 2006 are generated in a manner similar to that for the voltage limits 2012, 2014 of the draw portion 2002. FIG. 21 graphically depicts the output voltage of the optical sensor 1227 versus the volume of flush solution.

The upper voltage limit 2016 for the flush portion 2006 is a reverse exponential moving average of the output voltage of the optical sensor 1227 with a positive offset value. The upper voltage limit 2016 for the flush portion 2006 may be calculated utilizing the following formula:

$$ULF_i = ULF_{i+1}*(1-W_f) + (Xf_i + Sf)*Wf$$

Conversely, the lower voltage limit 2018 for the draw portion 2002 is a forward exponential moving average of the output voltage of the optical sensor 1227 with a negative offset value.

The lower voltage limit 2018 may be calculated using the following formula:

$$LLF_i = LLF_{i-1}*(1-W_f) + (Xf_i - Sf)*Wf$$

The following variables are used to calculate the upper voltage limit 2012 and the lower voltage limit 2014.
ULF$_i$=the flush cycle upper acceptance limit at data point "i" (volts).
ULF$_{i+1}$=the flush cycle upper acceptance limit at the next data point "i+1" (volts).
ULF$_n$=the flush cycle upper acceptance limit at the final data point (volts), ULF$_n$=Xf$_n$+Sf.
LLF$_i$=the flush cycle lower acceptance limit at data point "i" (volts).
LLF$_{i-1}$=the flush cycle lower acceptance limit at the previous data point "i−1" (volts).
LLF$_1$=the flush cycle lower acceptance limit at the first data point (volts), LLF$_1$=Xf$_1$−Sf.
Xf$_i$=the LED sensor voltage for the flush cycle at data point "i" (volts).
Xf$_1$=the LED sensor voltage for the flush cycle at the first data point (volts).
Xf$_n$=the LED sensor voltage for the flush cycle at the final data point (volts).
Vf$_i$=the calculated flush volume at data point "i" (mL), Vf$_i$=(Qf/60)*(tf$_i$−tf$_1$).
Vf$_n$=the calculated total flush volume (mL), Vf$_n$=(Qf/60)*(tf$_n$−tf$_1$).
Qf=the applied flush speed (mL/min).
tf$_1$=the start time for the flush cycle, i.e., when the pump begins running (sec).
tf$_n$=the stop time for the flush cycle, i.e., when the pump stops running (sec).
Sf=the user specified offset value for the flush cycle (volts), Sf>0.
Ff=the user specified fraction of the system dead volume for the flush cycle, Ff>0.
Wf=the calculated weighting factor for the flush cycle, Wf=2/(Nf+1).
Nf=the calculated number of moving data points for the flush cycle, Nf=Ff*DV/ΔVf.
DV=the sampling system dead volume (mL).
ΔVf=the incremental flush volume between successive data points (mL), ΔVf=Vf$_n$/(n−1).
n=the total number of data points comprising the flush cycle.

Thus, the equations above for the upper voltage limit 2016 and the lower voltage limit 2018 for the flush portion 2006 are a function of calculated volume flushed and may be stored into a memory accessible by a processor.

The user specified offset value Sf for the flush portion 2006 and the user specified fraction of the system dead volume Ff for the flush portion 2006 may be set depending on a particular test being performed, or the sensitivity required for testing a particular patient. Default values for the specified offset Sf and the dead volume Ff may be stored within the memory, but a caregiver may modify these values such that fewer error conditions are detected, thus reducing false positive error conditions.

Once the upper and lower voltage limits 2012, 2014 for the draw cycle 2002 and the upper and lower voltage 2016, 2018 for the flush cycle 2006 have been generated and stored, subsequent operation of the system 1000 may be evaluated based upon the output of the fluid flow sensor 1227 compared to the voltage limits 2012, 2014, 2016, and 2018 to detect malfunctions of the system 1000.

Subsequent operational cycles are defined by the following system control parameters:
Draw speed: Qdi=the syringe pump speed in the forward direction at time point "i" (mL/min).
Draw volume: Vd=the target volume of blood sample drawn into the IV set (mL).
Pause time: tp=the time needed to perform a diagnostic measurement on the blood sample (sec).
Flush speed: Qfi=the syringe pump speed in the reverse direction at time point "i" (mL/min).
Flush volume: Vf=the target volume of blood sample+flush solution flushed from the IV set (mL).

During operation of the system 1000, the draw speed Qdi and the flush speed Qfi may remain constant, or may vary over the draw portion 2002 and the flush portion 2006 of the draw and flush cycle 2000. Therefore, during operation, the of the system, the output of the optical sensor 1227 will be monitored over the course of draw and flush cycle 2000 to ensure that the voltage is between the upper and lower voltage limits 2012, 2014, 2016, 2018 during the draw portion 2002 and the flush portion 2006. It is additionally contemplated that the output of the optical sensor 1227 is monitored during the delay portion 2004 as well, since the volume of fluid drawn during the draw portion 2002 is known during the delay portion 2004.

During the draw portion 2002 of the draw and flush cycle 2000, a malfunction is detected if voltage output of the optical sensor 1227 at a particular point Xd$_i$ during the draw portion 2002 is above the upper voltage limit 2012 or below the lower voltage limit 2014.

Similarly, during the flush portion 2006 of the draw and flush cycle 2000, a malfunction is detected if the voltage output of the optical sensor 1227 at a particular point Xf$_i$ during the flush portion 2006 is above the upper voltage limit 2016 or below the lower voltage limit 2018.

Figure 22:
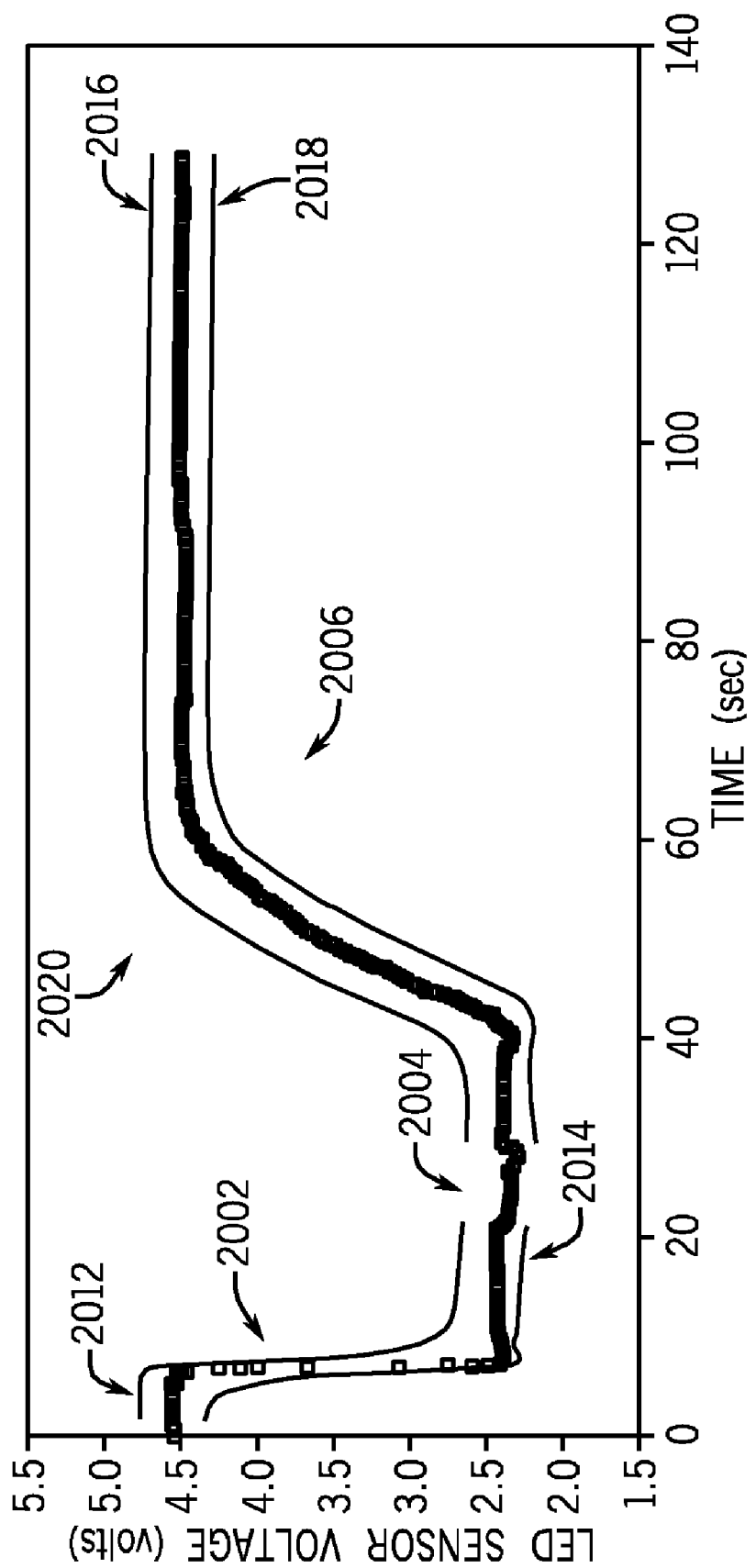
FIG. 22 is a graph showing the output voltage versus time for an optical sensor for use with the testing system also showing voltage limits the graph showing normal operations.

Turning now to FIG. 22 a graph 2020 depicting voltage output of the optical sensor 1227 over time is shown for a fluid pumping rate of about 1.5 mL/min and no malfunctions were detected. The upper and lower voltage limits 2012, 2016, 2014, 2018 depicted in FIG. 22 were generated as described above with a fluid pumping rate of about 3 mL/min. However, as shown in FIG. 22, by utilizing fluid volumes drawn or flushed to generate the voltage limits 2012, 2014, 2016, 2018, it is possible to vary the flow rates without exceeding the voltage limits 2012, 2014, 2016, 2018 so long as the actual volume flushed or drawn is generally equal to the expected volumes. Therefore, as the total draw volume for the example depicted in FIG. 22 is the expected 0.5 mL, and the flush volume is the expected 2.5 mL, the effect of operating the system at a slower fluid pumping rate simply results in the graph 2020 extending further along the time axis.

Figure 23:
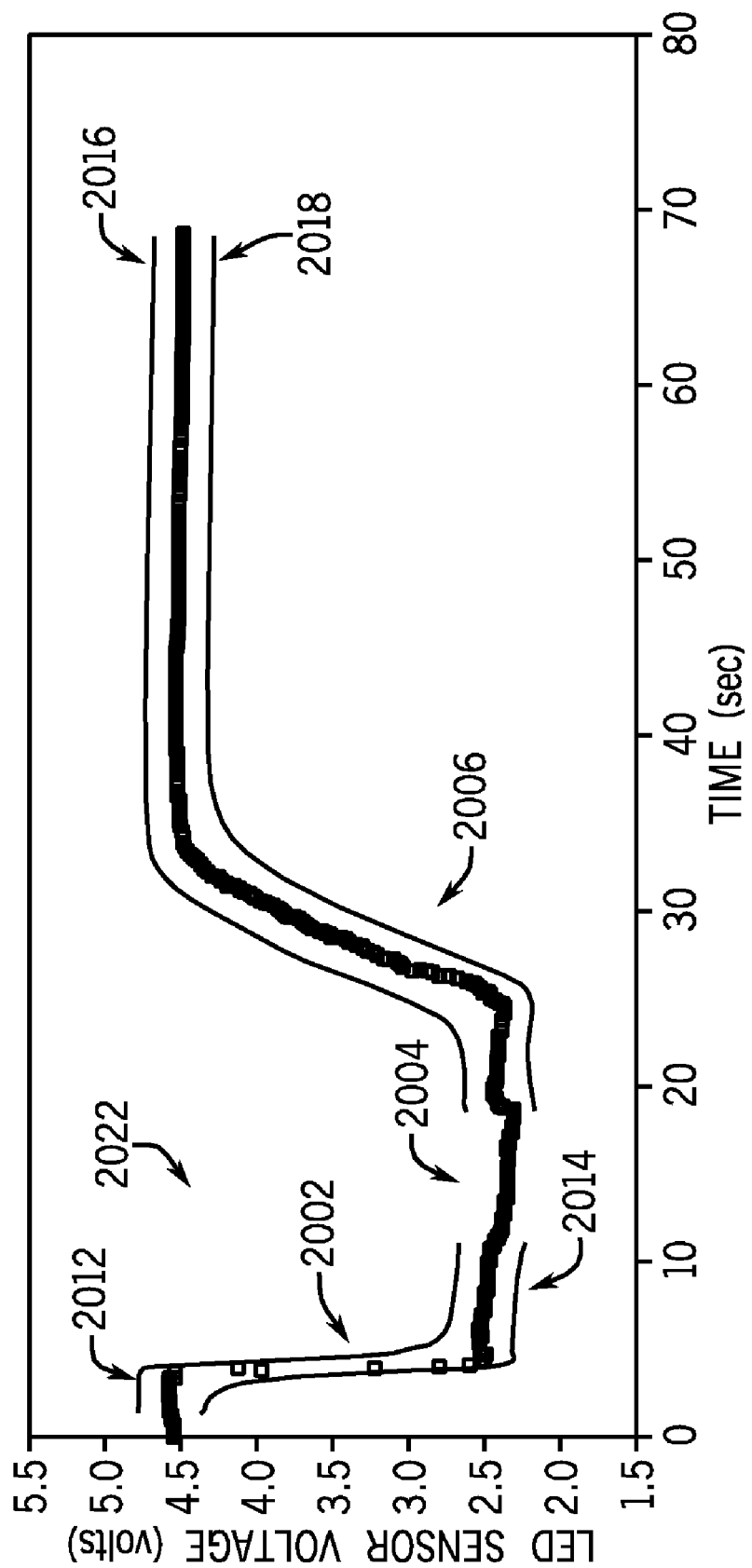
FIG. 23 is a graph showing the output voltage versus time for an optical sensor for use with the testing system also showing voltage limits the graph showing normal operations.

FIG. 23 shows a graph 2022 depicting voltage output of the optical sensor 1227 over time for a fluid pumping rate of about 3 mL/min and no malfunctions were detected. The upper and lower voltage limits 2012, 2016, 2014, 2018 depicted in FIG. 22 were generated as described above with a fluid pumping rate of about 3 mL/min, therefore the graph 2022 is similar to the graph 2020 shown in FIG. 22, except that the total time required for the cycle depicted in FIG. 23 is about half of the time required for the cycle depicted in FIG. 22.

Figure 24:
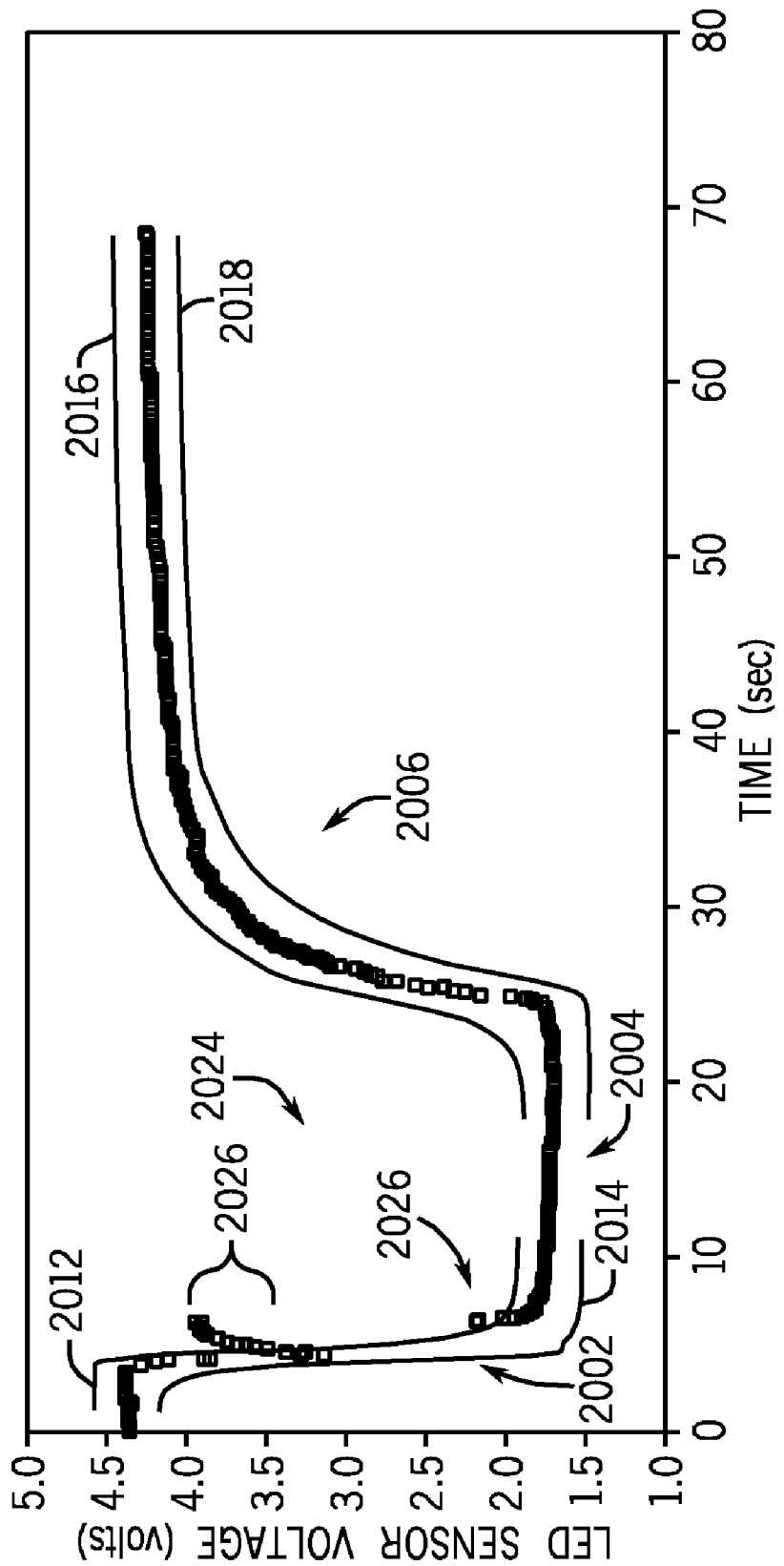
FIG. 24 is a graph showing the output voltage versus time for an optical sensor for use with the testing system also showing voltage limits the graph showing a potential occlusion during fluid drawing.

Referring next to FIG. 24, a graph 2024 depicting voltage output of the optical sensor 1227 over time is shown for a fluid pumping rate of about 3 mL/min and a potential malfunction 2026 detected during the draw portion 2002. The potential malfunction 2026 during the draw portion 2002 shows the voltage exceeding the upper voltage limit 2012. The potential malfunction 2026 may indicate that an occlusion has occurred within the system 1000. However, the occlusion in FIG. 24 had cleared up and the voltage output of the optical sensor 1227 at point 2027 once again resides between the upper voltage limit 2012 and the lower voltage limit 2014 of the draw portion 2002.

Figure 25:
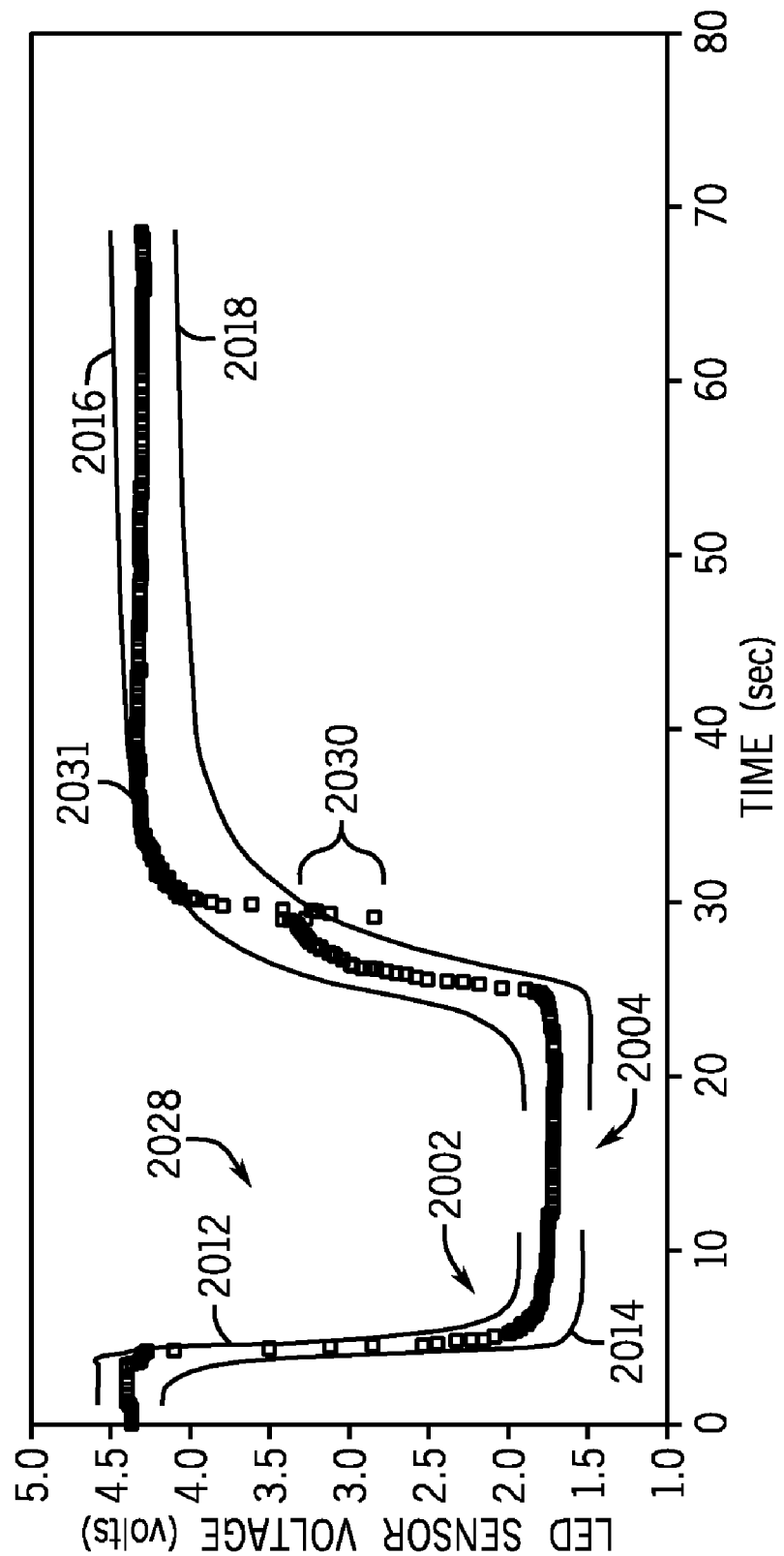
FIG. 25 is a graph showing the output voltage versus time for an optical sensor for use with the testing system also showing voltage limits the graph showing a potential occlusion during fluid flushing.

FIG. 25 depicts a graph 2028 that is similar to graph 2024 shown in FIG. 24, except that a potential malfunction 2030 is detected in the flush portion 2006. The graph 2028 depicts voltage output of the optical sensor 1227 over time is shown for a fluid pumping rate of about 3 mL/min. The potential malfunction 2030 shows the voltage both upper voltage limit 2016 and the lower voltage limit 2018 of the flush portion 2006 were exceeded by the voltage output of the optical sensor 1227. The potential malfunction 2030 may indicate that an occlusion has occurred within the system 1000. The occlusion shown in FIG. 25 had been remedied at point 2031 of the graph 2028 as the voltage output of the optical sensor 1227 once again resided between the upper voltage limit 2016 and the lower voltage limit 2018.

Figure 26:
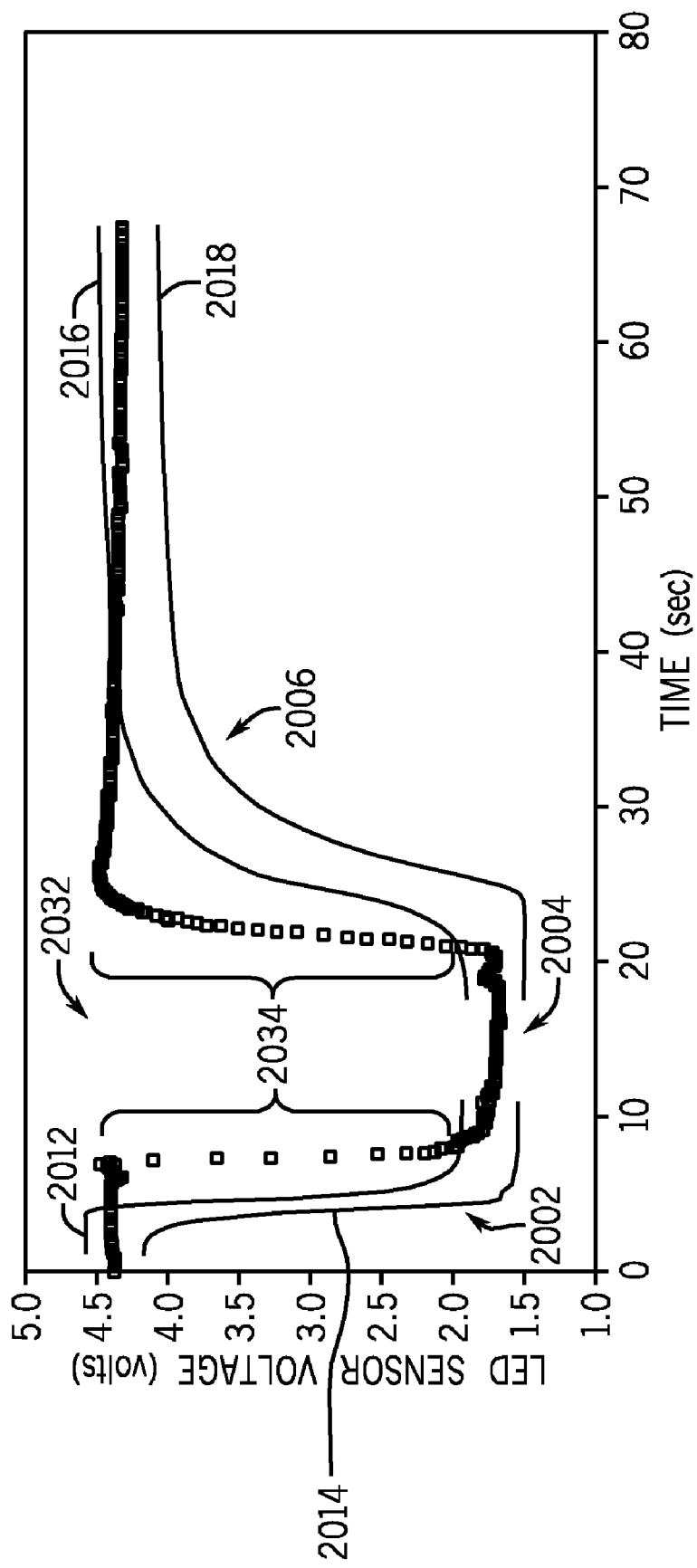
FIG. 26 is a graph showing the output voltage versus time for an optical sensor for use with the testing system also showing voltage limits the graph showing a potential pump rate malfunction.

Turning to FIG. 26, a graph 2032 shows a different type of malfunction from the occlusions depicted in FIGS. 24 and 25. The graph 2032 shows a potential malfunction 2034 that the upper voltage limit 2012 of the draw portion and the upper voltage limit 2016 of the flush portion 2006 have both been exceed by the output voltage of the optical sensor 1227. The potential malfunction 2034 shown in FIG. 26 is consistent with a pump rate that is about half of the expected flow rate, while the operating time of the pump is not extended, thus only about half of the expected fluid volume is drawn during the draw period 2002 and flushed during the flush period 2006. Thus, if the draw period 2002 had a target volume of 0.5 mL, only 0.25 mL would actually be drawn into the system 1000 as shown in FIG. 26, due to the reduced pump rate.

Similarly, if the flush period 2006 had a target volume of 2.5 mL, only 1.25 mL would be flushed from the system 1000 as shown in FIG. 26. The potential malfunction 2034 is important to detect, as inadequate draw volumes may result in inaccurate testing results by the system 1000.

Figure 27:
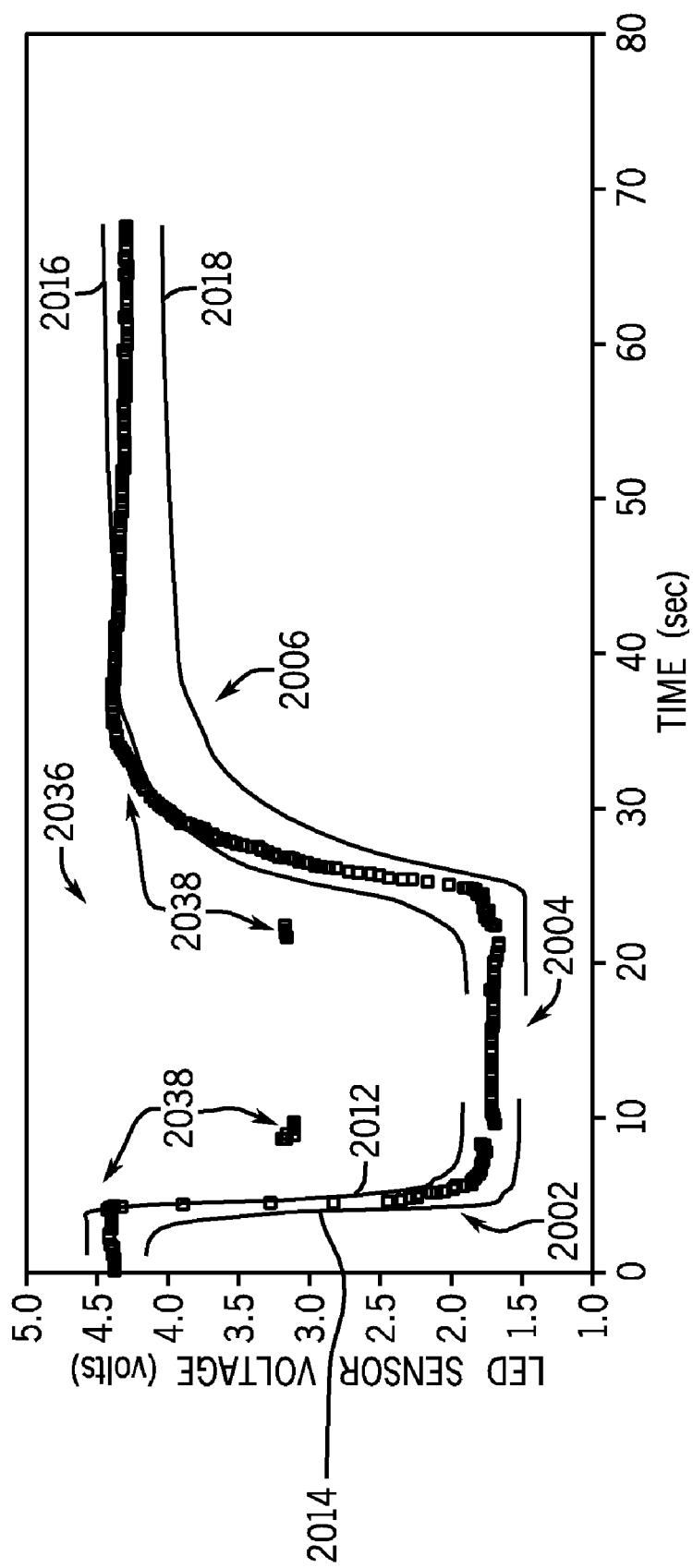
FIG. 27 is a graph showing the output voltage versus time for an optical sensor for use with the testing system also showing voltage limits the graph showing a potential presence of air within the system.

Finally, FIG. 27 depicts a graph 2036 showing yet another type of potential malfunction 2038 indicative of the presence of air within the system 1000. The graph 2036 shows the potential malfunction 2038 as a brief increase in voltage during both the draw cycle 2002 and another during the flush cycle 2006. The voltage level at the potential malfunction is less than the voltage output of the flush solution, but is more than the voltage output of the fluid being drawn. Therefore, the system 1000 is capable of recognizing the voltage output of the potential malfunction 2038 as being the voltage the optical sensor 1227 outputs in the presence of air.

One skilled in the art will appreciate that other sensors in the system, such as sensor 211, or other types of sensors besides the optical sensor 1227 shown can be used to generate the signals needed to carry out and utilize the present invention. Some other types of sensors that could be used without detracting from the invention include without limitation electrochemical sensors, conductivity sensors and ultrasonic sensors.

While the foregoing has described what is considered to be the best mode and/or other examples, it is understood that various modifications may be made and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true scope of the subject matter. Therefore, the subject matter is not limited to the specific details, exhibits and illustrated examples in this description. It is intended to protect any and all modifications and variations that fall within the true scope of the advantageous concepts disclosed herein.

I claim:

1. A method of monitoring performance of a fluid testing system having a sensor, a patient connection adapted to connect the system to a patient to collect a fluid sample, a pump, a processor in communication with a memory, and a flushing fluid connection adapted to connect the system to a flushing fluid to flush the system after a fluid test, the method comprising:

drawing a fluid sample from the patient via the patient connection using a pump of the testing system to draw the fluid sample from the patient to the testing system:

generating a voltage output of a sensor indicative of a fluid present at the sensor;

comparing the voltage output of the sensor during the drawing of the fluid sample to an upper fluid volume drawn based voltage limit and a lower fluid volume drawn based voltage limit stored within a memory in communication with a processor;

flushing the system with a flushing fluid using the pump of the testing system to flush the flushing fluid from the testing system;

comparing the voltage output of the sensor during the flushing of the flushing fluid to an upper fluid volume flushed based voltage limit and a lower fluid volume flushed based voltage limit stored within the memory in communication with the processor; and generating an alert if at least one of the voltage output during the drawing of the fluid sample is outside of the lower fluid volume drawn based voltage limit and the upper volume drawn based voltage limit and the voltage output during the flushing of the flushing fluid is outside of the lower fluid volume flushed based voltage limit and the upper fluid volume flushed based voltage limit.

2. The method of claim 1, wherein the upper fluid volume drawn based voltage limit is generated using a forward exponential moving average of the voltage output of the sensor.

3. The method of claim 1, wherein the lower fluid volume drawn based voltage limit is a generated using a reverse exponential moving average of the voltage output of the sensor.

4. The method of claim 1, wherein the upper fluid volume flushed based voltage limit is generated using a reverse exponential moving average of the voltage output of the sensor.

5. The method of claim 1, wherein the upper fluid volume flushed based voltage limit is a generated using a forward exponential moving average of the voltage output of the sensor.

6. The method of claim 1, wherein the alert indicates at least one of an occlusion during the drawing the fluid sample, an occlusion during the flushing the system, presence of air in the system, and a pump rate malfunction.

7. The method of claim 1, wherein the upper fluid volume drawn based voltage limit and the lower fluid volume drawn based voltage limit stored within the memory are generated on the fluid testing system.

8. The method of claim 1, wherein the upper fluid volume flushed based voltage limit and the lower fluid volume flushed based voltage limit stored within the memory are generated on the fluid testing system.

9. The method of claim 1, wherein the step of generating a voltage output of a sensor is done by an optical sensor disposed in the testing system.

10. The method of claim 1, wherein during one of the drawing step and the flushing step the testing system operates the pump at a generally constant pumping rate.

11. A method of generating voltage output limits for a fluid draw of a fluid testing system having an optical sensor, a patient connection adapted to connect the system to a patient to collect a fluid sample, a pump, and a processor in communication with a memory, the method comprising:
   drawing a known quantity fluid sample using a pump of the testing system to draw the fluid sample to the testing system;
   generating a plurality of voltage outputs of an optical sensor indicative of a fluid present at the optical sensor periodically during the drawing of the fluid sample;
   calculating an upper voltage limit utilizing a forward exponential moving average of the plurality of voltage outputs and a positive offset value; and
   calculating a lower voltage limit utilizing a reverse exponential moving average of the plurality of voltage outputs and a negative offset value.

12. The method of claim 11, wherein the positive offset value may vary based upon a type of test being performed by the fluid testing system.

13. The method of claim 11, wherein the pump of testing system operates at a generally constant pumping rate during the drawing the known quantity fluid sample.

14. The method of claim 11, wherein the upper voltage limit is a function of volume drawn into the system at a particular time during the drawing.

15. The method of claim 11, wherein the lower voltage limit is a function of volume drawn into the system at a particular time during the drawing.

16. A method of generating voltage output limits for a fluid flush of a fluid testing system having an optical sensor, a patient connection adapted to connect the system to a patient to collect a fluid sample, a pump, and a processor in communication with a memory, the method comprising:
   flushing a known quantity of fluid from the fluid testing system using a pump of the testing system to flush the fluid;
   generating a plurality of voltage outputs of an optical sensor indicative of a fluid present at the optical sensor periodically during the flushing of the fluid;
   calculating an upper voltage limit utilizing a reverse exponential moving average of the plurality of voltage outputs and a positive offset value; and
   calculating a lower voltage limit utilizing a forward exponential moving average of the plurality of voltage outputs and a negative offset value.

17. The method of claim 16, wherein the positive offset value may vary based upon a type of test being performed by the fluid testing system.

18. The method of claim 16, wherein the pump of testing system operates at a generally constant pumping rate during the flushing the known quantity of fluid.

19. The method of claim 16, wherein the upper voltage limit is a function of volume flushed from the system at a particular time during the flushing.

20. The method of claim 16, wherein the lower voltage limit is a function of volume flushed from the system at a particular time during the flushing.

* * * * *